United States Patent
Carlini et al.

(10) Patent No.: US 11,058,397 B2
(45) Date of Patent: Jul. 13, 2021

(54) METHOD FOR QUANTIFYING THE ELASTICITY OF A MATERIAL BY ULTRASOUNDS

(71) Applicant: Esaote S.p.A., Genoa (IT)

(72) Inventors: Davide Carlini, Genoa (IT); Fulvio Biordi, Genoa (IT)

(73) Assignee: Esaote S.p.A., Genoa (IT)

(*) Notice: Subject to any disclaimer, the term of this patent is extended or adjusted under 35 U.S.C. 154(b) by 29 days.

(21) Appl. No.: 15/536,269

(22) PCT Filed: Dec. 29, 2015

(86) PCT No.: PCT/IB2015/060020
§ 371 (c)(1),
(2) Date: Jun. 15, 2017

(87) PCT Pub. No.: WO2016/108178
PCT Pub. Date: Jul. 7, 2016

(65) Prior Publication Data
US 2017/0340310 A1    Nov. 30, 2017

(30) Foreign Application Priority Data
Jan. 2, 2015 (IT) .......................... GE2015A000001

(51) Int. Cl.
*A61B 8/00* (2006.01)
*A61B 8/08* (2006.01)
(Continued)

(52) U.S. Cl.
CPC .............. *A61B 8/485* (2013.01); *A61B 5/318* (2021.01); *A61B 8/0825* (2013.01); *A61B 8/463* (2013.01);
(Continued)

(58) Field of Classification Search
CPC ..... A61B 5/0402; A61B 8/485; A61B 8/0825; A61B 8/463; A61B 8/469; A61B 8/5223;
(Continued)

(56) References Cited

U.S. PATENT DOCUMENTS 5,606,971 A * 3/1997 Sarvazyan ............... A61B 8/08
600/438
5,735,281 A * 4/1998 Rafter ..................... A61B 5/352
600/458

(Continued)

OTHER PUBLICATIONS

Brian J Fahey et al., "A Novel Motion Compensation Algorithm for Acoustic Radiation Force Elastography", IEEE Transactions on Ultrasonics, Ferroelectrics, and Frequency Control;, IEEE US, vol. 55, No. 5, May 2, 2008, pp. 1095-1111, XP011215068.*

(Continued)

*Primary Examiner* — Carl H Layno
*Assistant Examiner* — Michael J Lau
(74) *Attorney, Agent, or Firm* — Dickinson Wright PLLC

(57) ABSTRACT

A method for quantifying the elasticity of a material by ultrasounds, comprising the generation of one excitation point, for generating a shear wave, a measurement of the shear wave at a plurality of lines of sight placed in a region of interest at different predetermined distances from the first excitation point, the calculation of the speed of the measured shear wave and the assessment, by calculation, of a mean stiffness value of the material in the region of interest on the basis of the measured speed of the shear wave. In the acquired image, a second excitation point is defined, in such a position that the region of interest is interposed between the first excitation point and the second excitation point. The method for the second excitation point is carried out, for calculating the speed of the shear wave for the second excitation point, and the assessment by calculation of the mean stiffness value is carried out on the basis of the average (Continued)

between the speed of the shear wave measured for the first excitation point and the speed of the shear wave measured for the second excitation point.

31 Claims, 15 Drawing Sheets

(51) Int. Cl.
    *G01S 7/52*     (2006.01)
    *A61B 5/318*     (2021.01)

(52) U.S. Cl.
    CPC ............ *A61B 8/469* (2013.01); *A61B 8/5223* (2013.01); *A61B 8/5276* (2013.01); *G01S 7/52022* (2013.01); *G01S 7/52042* (2013.01); *G01S 7/52085* (2013.01); *A61B 8/543* (2013.01)

(58) Field of Classification Search
    CPC ... A61B 8/5276; A61B 8/543; G01S 7/52022; G01S 7/52042; G01S 7/52085
    USPC .................................................. 600/301, 437
    See application file for complete search history.

(56) References Cited

U.S. PATENT DOCUMENTS

| | | | | |
|---|---|---|---|---|
| 6,270,459 | B1* | 8/2001 | Konofagou | A61B 5/0053 600/449 |
| 6,508,768 | B1* | 1/2003 | Hall | A61B 8/08 600/443 |
| 7,444,875 | B1* | 11/2008 | Wu | A61B 8/08 73/602 |
| 8,428,687 | B2* | 4/2013 | Konofagou | G01S 7/52071 600/407 |
| 2003/0045796 | A1* | 3/2003 | Friedman | A61B 8/543 600/450 |
| 2005/0165306 | A1* | 7/2005 | Zheng | A61B 8/485 600/437 |
| 2006/0287596 | A1* | 12/2006 | Johnson | A61B 8/14 600/437 |
| 2008/0285819 | A1* | 11/2008 | Konofagou | A61B 8/0883 382/128 |
| 2009/0056453 | A1* | 3/2009 | McAleavey | G01N 29/449 73/597 |
| 2010/0240994 | A1* | 9/2010 | Zheng | A61B 8/463 600/438 |
| 2010/0286516 | A1* | 11/2010 | Fan | A61B 8/08 600/438 |
| 2010/0286520 | A1* | 11/2010 | Hazard | G01S 7/52042 600/439 |
| 2011/0130800 | A1* | 6/2011 | Weinstein | A61B 8/4254 607/17 |
| 2011/0306884 | A1* | 12/2011 | Tanigawa | A61B 8/5223 600/443 |
| 2011/0319756 | A1* | 12/2011 | Zheng | G01S 7/52036 600/438 |
| 2012/0089019 | A1* | 4/2012 | Fan | A61B 8/485 600/437 |
| 2012/0136250 | A1* | 5/2012 | Tabaru | G01S 7/52026 600/438 |
| 2012/0269416 | A1* | 10/2012 | Waki | A61B 8/483 382/131 |
| 2013/0028536 | A1* | 1/2013 | Hazard | A61B 8/5276 382/275 |
| 2013/0031981 | A1* | 2/2013 | Montaldo | G01S 7/52036 73/606 |
| 2013/0123630 | A1* | 5/2013 | Freiburger | A61B 8/08 600/443 |
| 2013/0237820 | A1* | 9/2013 | Vappou | A61B 8/0858 600/438 |
| 2013/0245442 | A1* | 9/2013 | Hazard | A61B 8/485 600/438 |
| 2013/0261429 | A1* | 10/2013 | Lee | A61B 5/0035 600/411 |
| 2014/0018679 | A1* | 1/2014 | Chen | G01S 7/52042 600/438 |
| 2014/0046173 | A1* | 2/2014 | Greenleaf | G16H 50/30 600/411 |
| 2014/0058266 | A1* | 2/2014 | Call | A61B 8/5207 600/448 |
| 2014/0276046 | A1* | 9/2014 | Kim | A61B 8/08 600/438 |
| 2015/0313573 | A1* | 11/2015 | Liu | A61B 8/5207 600/399 |

OTHER PUBLICATIONS

International Search Report dated Sep. 17, 2015 which issued in PCT Application No. PCT/IB2015/060020, including English Translation.

* cited by examiner

METHOD FOR QUANTIFYING THE ELASTICITY OF A MATERIAL BY ULTRASOUNDS

BACKGROUND OF THE INVENTION

The present invention relates to a method for quantifying the elasticity of a material by ultrasounds, comprising the following steps:

a) acquiring an ultrasound image;
b) defining a region of interest in the image;
c) defining a first excitation point in the acquired image;
d) generating at least one acoustic disturbance ultrasound beam for the first excitation point, for generating at least one shear wave, which shear wave originates in the first excitation point and has a direction of propagation substantially perpendicular to the direction of propagation of the ultrasound beam, the first excitation point being positioned in such a manner that the shear wave passes through the region of interest;
e) measuring the displacement of the image pixels induced by the shear wave passing through the region of interest at a plurality of lines of sight placed in the region of interest at different predetermined laterally staggered distances from the first excitation point;
f) calculating the speed of the measured shear wave;
g) assessing, by calculation, a mean stiffness value of the material in the region of interest on the basis of the measured speed of the shear wave.

The material in question can be of any type, both non biological type, as in the case of non-destructive testing, and composed of biological tissues.

Elasticity of soft biological tissues has been used for evaluating possible pathological conditions since the dawning of medicine. The use of manual palpations for evaluating the health condition of the tissues is still used commonly in routine medical examinations. For example the presence of rigid masses found during routine breast examinations is often an early indication of breast cancer. Manual palpation methods however are relatively little objective and are limited to surface anatomical structures.

The methods for quantifying the elasticity or for the comparative measurement of biological tissues by ultrasounds allow deep-tissue elasticity to be measured in the body under examination, are reliable and therefore are used in clinical practice.

Unlike the traditional ultrasound imaging, such as for example B-mode, that allows images to be acquired where tissues with different acoustic properties are distinguished, the methods measuring the elasticity allow tissues with different mechanical properties to be distinguished. To do this, such methods carry out an excitation of the tissues and monitor the strain response, which is related to tissue elasticity.

A type of elasticity measurement methods provides to use transverse waves, or shear waves, generated after an excitation, and are defined as Shear Wave Elasticity Imaging (SWEI). These methods provide to generate shear waves in the tissue following an acoustic disturbance, called as shock disturbance, of the first excitation point applied by the ultrasound probe, and consequently to monitor the shear waves in the regions of interest placed outside the area or the point of excitation. By measuring the displacements over time of the image or of the pixels of the image or of the pixels of a Line of Sight at a plurality of lateral positions separated by a known distance from the excitation source, it is possible to estimate the shear wave speed.

Actually the measurement is indirect since the method detects the propagation speed of the shear wave in a direction substantially orthogonal to the acoustic shock disturbance of the excitation point.

The relation between speed of such shear wave and the elasticity is approximate and it depends on some assumptions about the density of the tissue under examination.

The tissue elasticity is proportional to the propagation speed $\rho$ of the shear wave $V_s$, according to the following formula:

$$E \approx 3\rho V_s^2$$

wherein it is assumed that $\rho \approx 1$, namely that tissue density is unit quantity.

The document U.S. Pat. No. 5,606,971 describes a SWE method, that uses a focused ultrasound transducer which induces shear waves in a tissue by sending modulated ultrasonic pulses. The shear wave of the frequency of the modulating signal is detected. The mechanical properties of tissues under examination are evaluated on the basis of the measured values of speed and attenuation of shear waves.

A subset of such methods is the one defined as pSWE (Point Shear Wave Elasticity), where, instead of an image, a point measurement generally averaged in the region of interest is generated.

A problem of the known methods derives from the possibility of the probe and/or patient moving during the examination. Such movements during acquisition can be substantially considered of two different types: transversal, i.e. along the direction of propagation of the transversal wave, due, for example, due to a translation or shift of the probe on skin of the patient or a rotation of the probe by small angles on the plane of the image or longitudinal, i.e. along the direction of propagation of the ultrasound beam, caused, for example, by a different relative position of the probe with reference to the patient due to a different pressure of the hand holding the probe or patient breathing.

In both cases the measurement is altered: in presence of a transversal movement the wave is detected slightly beforehand or slightly later, depending on the direction of rotation or of translation of the probe; in presence of a longitudinal movement the reconstructed signal contains also the effect of such movement consisting in an erroneous ramp trend superimposed on the wave. This leads to a calculation of the shear wave propagation speed not corresponding to reality, and therefore to a distorted estimation of tissue elasticity.

SUMMARY OF THE INVENTION

The present invention aims at overcoming the drawbacks of the currently known methods by a method such as described hereinbefore, which further comprises the following steps, carried out before step g):

h) defining in the acquired image a second excitation point in such a position that the region of interest is interposed between the first excitation point and the second excitation point;

i) carrying out steps d) to f) for the second excitation point, for calculating the speed of the shear wave for the second excitation point;

and wherein the calculation of the mean stiffness value as in step g) is carried out on the basis of the average between the speed of the shear wave measured for the first excitation point and the speed of the shear wave measured for the second excitation point.

According to an improvement, longitudinal movement is compensated by subtracting from each displacement of image pixels a curve having a correction slope.

The correction slope is advantageously calculated by making a linear fitting between displacements related to subsequent lines of sight.

According to a preferred embodiment, the correction slope for one line of sight is obtained by summing all the correction slopes calculated for the previous lines of sight. The first correction slope is typically calculated on a reference displacement as no shear waves due to preceding shock pulses exists.

The method of the present invention therefore allows a reliable measurement of the elasticity of the material under examination to be obtained, particularly of the biological tissues under examination, by correcting anomalies due to the movement, in particular due to the mutual rotation of the probe with respect to the patient or vice versa on the image plane. The fact of providing two excitation points on two opposite sides of the region of interest, allows movement errors to be compensated since, if the detection of the shear wave is anticipated for the measurement corresponding to the first excitation point, it is delayed for the measurement corresponding to the second excitation point and vice versa. This is obviously valid for movements of the probe and/or of the patient that are small and always having the same direction during the examination.

In one embodiment the measurement of the shear wave provides to measure the mean displacement over time of the tissue along each line of sight in the considered gate and to identify the peak of the mean displacement measured for each line of sight.

The displacement is a mean displacement since it is averaged in the space, by grouping the displacement measurement between near pixels. On each line of sight, the measurement of the displacement is repeated over time to form a sample curve representing the passage of the shear wave.

Preferably such curve is filtered by a moving mean such to eliminate noise.

Therefore the peak of the measured mean displacement is defined to find the shear wave propagation speed: the peak instant on each line of sight related to the known distance of the lines of sight from each other allows the propagation speed to be calculated. Identifying the peak is the most simple and advantageous operation, but as an alternative it is possible to consider other significant points of the curve such as for example the maximum slope point or the correlation between the curves or the difference between curves.

Therefore the displacements inside the region of interest along the lines of sight are considered, such to reconstruct the shear wave propagation pattern by the measurement of all the lines of sight.

In one embodiment, the measurement of the mean displacement over time of the tissue along each line of sight provides for each line of sight the acoustic disturbance of the first or second excitation point and the corresponding generation of a shear wave, and a plurality of repeated measurements on the line of sight under examination.

Therefore the examination is structured in repeated acquisition sequences, and each sequence comprises an acoustic disturbance of the excitation point and a measurement of the displacement of the pixels related to a single line of sight or a plurality of lines of sight acquired in parallel. The measurement easily occurs line by line and therefore it is necessary a shock acoustic disturbance for each of the measurements on the different lines of sight acquired individually or in parallel.

For example it is possible to acquire one line of sight a time or two or four lines of sight a time in parallel, with standard B-mode imaging techniques.

In a further embodiment for each line of sight, before the acoustic disturbance of the excitation point, one or more reference measurements on the line of sight under examination are made.

Thus the displacement on the line of sight can be measured in relation to a reference condition where the tissue is not disturbed by the passage of the shear wave.

According to one embodiment, between the last measurement on a line of sight and the first measurement on the following line of sight, both reference or tracking one, there is provided a pause period as detailed hereinafter.

Such characteristic has a double advantage of allowing hardware to be prepared to perform a new acoustic disturbance, and at the same time of allowing the probe and the tissues to cool.

According to one embodiment, the measurement of the mean displacement over time of the tissue along the line of sight under examination provides to calculate the complex cross-correlation between each measurement and a reference measurement.

The pixels on each line of sight form a one-dimensional image quite stable in absence of shear waves, only affected by noise. When the shear wave is generated, such pixels translate along the line of sight due to the movement induced by the passage of the shear wave. Such displacement is measured by calculating the cross-correlation between the one-dimensional image at an instant and the one-dimensional image chosen as a reference, acquired before generating the shear wave.

Preferably cross-correlation is carried out by grouping the displacement measurement between near pixels, that is by a window that is translated along the line of sight inside the region of interest. The single resulting values then are averaged, obtaining the measurement of the mean displacement of the tissue not affected by noise as much as possible. Longitudinal movements can optionally be corrected by subtracting a ramp as described below.

In a further embodiment the calculation of the measured shear wave speed is carried out by identifying for each line of sight the instant corresponding to the peak of the cross-correlation in relation to the distance of the line of sight from the excitation point.

Therefore two distinct peak instants are defined, corresponding to the measurement carried out for the first excitation point and the measurement carried out for the second excitation point respectively.

The two distinct instants measured for the two excitation points are preferably averaged, such to find a mean peak time instant.

The elasticity value is calculated on the basis of the wave propagation speed calculated on the basis of the peak mean time instants and the distances between the lines of sight. By considering a plurality of lines of sight, the mean peak instants for each line of sight are placed in a graph with the time on the ordinate and space, or distance between lines of sight on the abscissa. Therefore the straight line that is the best approximation of the plotted values is traced, by known methods such as the least squares or the like, and the slope of the defined straight line corresponds to the calculated propagation speed.

According to a further embodiment, the data detected by the measurement of the shear wave are processed for filtering possible artifacts.

Preferably such processing is carried out before the calculation of the displacement on each line of sight and the following calculation of the shear wave propagation speed.

The present invention further relates to a method according to one or more of the preceding claims where the acquired image is displayed showing the region of interest, the first excitation point and/or the second excitation point being further displayed on the acquired image.

The present invention further relates to a method for quantifying the elasticity of biological tissues by ultrasounds as mentioned hereinbefore, where the acquired image is displayed, the excitation point being displayed on the acquired image.

This is a great help for the user, who immediately sees the origin of the shear wave.

This has many advantages, among which the possibility of making an immediate evaluation of the correctness of the position of the region of interest in relation to the excitation point and the evaluation of the correctness of the position of the excitation point in relation to the tissues. It is possible to accidentally carry out an excitation of a wrong point, such as for example a vessel, an interface area etc, such that the shear wave is not generated in the proper manner. In this case the error is clearly visible to the user, who can correct immediately the setting of the examination.

In one embodiment, an ECG signal is recorded and the generation of ultrasound beams and the measurement of the displacement of pixels in the image induced by the shear wave passing through the region of interest are synchronized with the ECG signal.

Thus the method can perform a triggering on the heartbeat, in order to try to suppress as much as possible the movement-related artifacts, for which the pSWE is very sensitive.

This embodiment can be used for the measurement of the elasticity of any biological tissue involved by the cardiac movement, and it is particularly advantageous in relation to the measurement on the left part of the liver, that is the liver part affected by the heartbeat.

The aim is to provide an elasticity measurement not only as regards the right region which is the most easy to be reached, but also as regards the left side that today is less analyzed, except invasively when possible or necessary.

The interest for the left part of the liver derives from the need, for a correct and complete diagnosis, of knowing the general condition of the liver in various diseases.

Such general outline can be obtained by making biopsies that are very invasive, require a lot of time and are expensive since they require hospitalization and to keep the patient under control for a time directly proportional to the number of taken samples. The average time is a whole day and method is expensive due to the necessary time and materials.

As an alternative, in the ideal case, the general outline can be obtained on the basis of general data about the elasticity both of the right lobe of the liver, more easy to be reached both by biopsy and by ultrasound examinations, and of the left lobe. Its motility derives from being close to the heart, which is due also to breathing and/or movement of the patient torso.

With the patient lying down and asked to stop breathing, the breathing and/or movement effects of the patient torso are completely annulled.

As regards the influence part by the heart beat it is on the contrary necessary to develop appropriate actions compensating for the "deleterious" effect of the cardiac motion on the measurement of pSWE, that is considerably affected by the movement, which leads to the occurrence of great artifacts that prevent, if not avoided/properly eliminated, a reliable and repeatable measurement of the liver elasticity from being obtained.

According to an improvement, the measured displacement of the image pixels induced by the shear wave passing through the region of interest is filtered for removing movement-related artifacts.

This allows an ad hoc management of the signal to be carried out in order to eliminate or reduce the possible residual movement-related artifact.

According to a further improvement, the filtering provides to emit a first acoustic disturbance ultrasonic beam, to analyse the influence of the heart movement on the measured displacement of the image pixels, to emit a second acoustic disturbance ultrasonic beam and to apply to the measured displacement of the image pixels a compensation processing based on the influence of the heart movement detected after the first ultrasonic beam.

This is a kind of iterative method that allows firstly the effects of the movement-related artifact on a test signal to be known, in order to later process a correct compensation action for properly "reading" the following signal.

This is valid in case of absence of arrhythmic heart events just in the moment of the analysis of the first and second shots, or emitted ultrasonic beam (very acceptable hypothesis). The absence of voluntary movement and breathing activity for the time for the double acquisition and analysis can be on the contrary handled by the patient.

In order to increase the filtering accuracy it is possible to use more than two shots, still providing the need for the absence of possible arrhythmias, absence of torso movement and the breath hold for time necessarily longer than the "simple" case of two shots and analysis.

It is possible to use technologies based on adaptive neural networks aiming at an empiric analysis of the artifact and at generating the algorithm for correcting it. The use of such technologies based on neural networks allows the possibility or capacity of a correct correction/elimination/compensation of the cardiac motion-related artifact to be based on the calculation capacity or speed of the used system. Such compensation is repeatable on the same patient just due to the reiteration of the cardiac motion itself.

These and other characteristics and advantages of the present invention will be more clear from the following description of some embodiments shown in the annexed drawings wherein:

DETAILED DESCRIPTION

Figure 1:
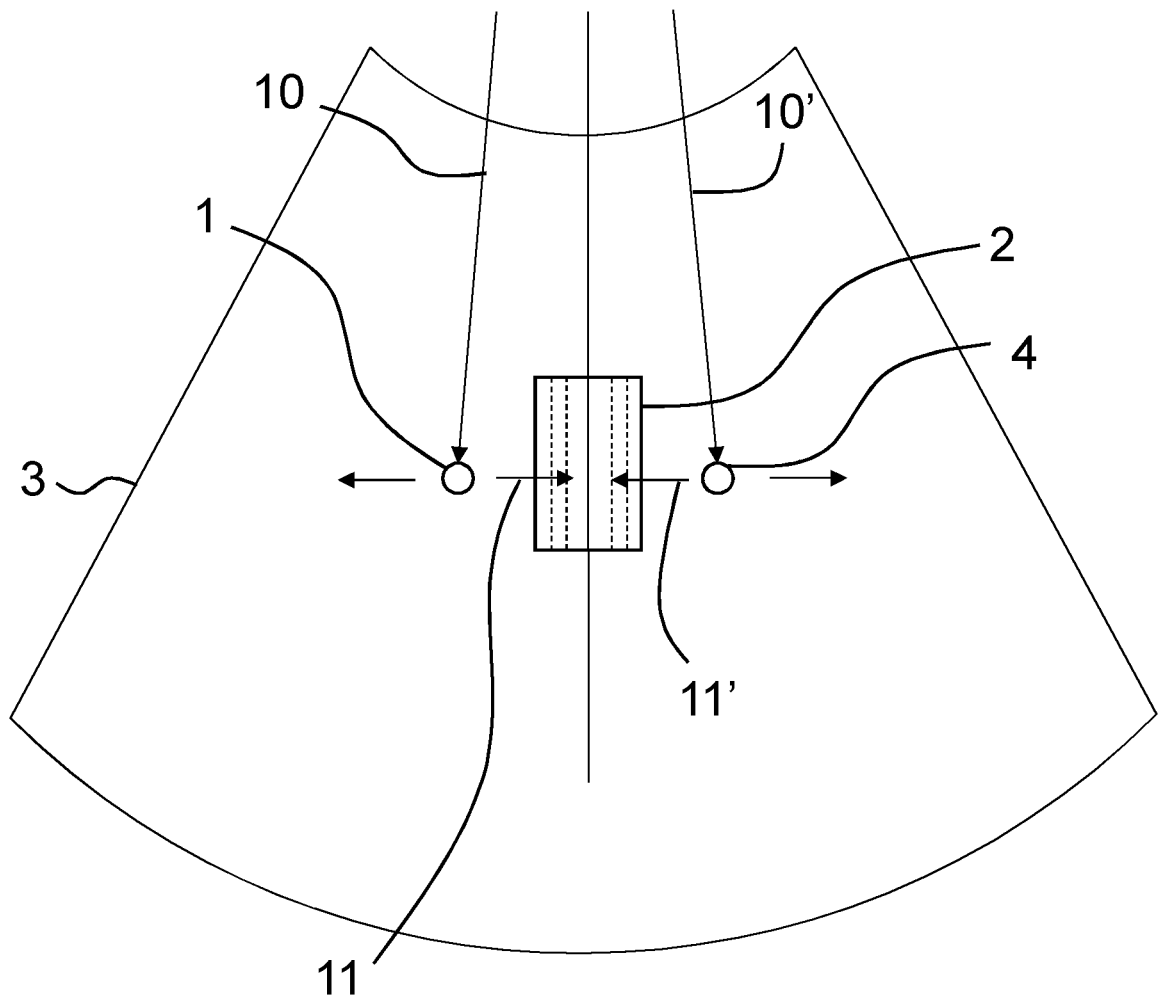
FIG. 1 is a possible display graphical interface.

FIG. 1 shows the interface of the method according to the present invention, which interface shows a B-mode ultrasound image 3. On the B-mode image the user defines a region of interest 2 through a gate, in which region of interest the tissue elasticity is desired to be indirectly measured.

The region of interest 2 may have any shape, preferably a rectangular shape or as a section of an annulus, and preferably it has a predetermined size for the end user. The user can place the region of interest 2 where he/she desires, preferably only in one portion of the image defined in the development step, such to avoid areas not suitable for the measurement, such as for example areas of the image that are too deep or too superficial.

During the dedicated acquisition, the B-mode image is still, or "frozen", and it can be removed from such condition only after producing the numerical result.

Therefore the user, once defining the region of interest 2, starts the measurement; the image is made as still, and the special insonification/acquisition is carried out for estimating the shear wave. Once such step has ended, the data are processed and the obtained result is displayed on the monitor.

Once a measurement has ended, the image can be "unfrozen" such to allow a new shot and a new acquisition, till leaving the mode.

Once the region of interest 2 is defined, a first excitation point 1 is defined within the acquired B-mode image 3.

Therefore a focused ultrasonic beam 10 is generated for the acoustic disturbance of the first excitation point 1, to generate a shear wave 11. The shear wave 11 originates in the first excitation point 1 and has a propagation direction substantially perpendicular to the direction of propagation of the ultrasonic beam 10, in the two opposite departing directions denoted by the arrows in the figure. The first excitation point 1 is placed such that the shear wave 11 passes through the region of interest 2.

The generated shear wave 11 is measured at a plurality of lines of sight placed inside the region of interest 2 at different predetermined distances from the first excitation point 1. The figure shows the line of sight under examination, while the other lines of sight are broken lines.

By the measurement of the passage of the shear wave on all the lines of sight the propagation speed of the measured shear wave is calculated.

Therefore a second excitation point 4 is defined within the acquired B-mode image 3, in such a position that the region of interest 2 is interposed between the two excitation points 1 and 4.

Also for the second excitation point 4 a shock acoustic disturbance 10' is performed, for generating a further shear wave 11', which passes through the region of interest 2 in a direction opposite to the direction of the shear wave 11 of the first excitation point 1 passing through the region of interest 2.

Also such further wave is measured on all the lines of sight and its propagation speed is calculated.

Figure 2:
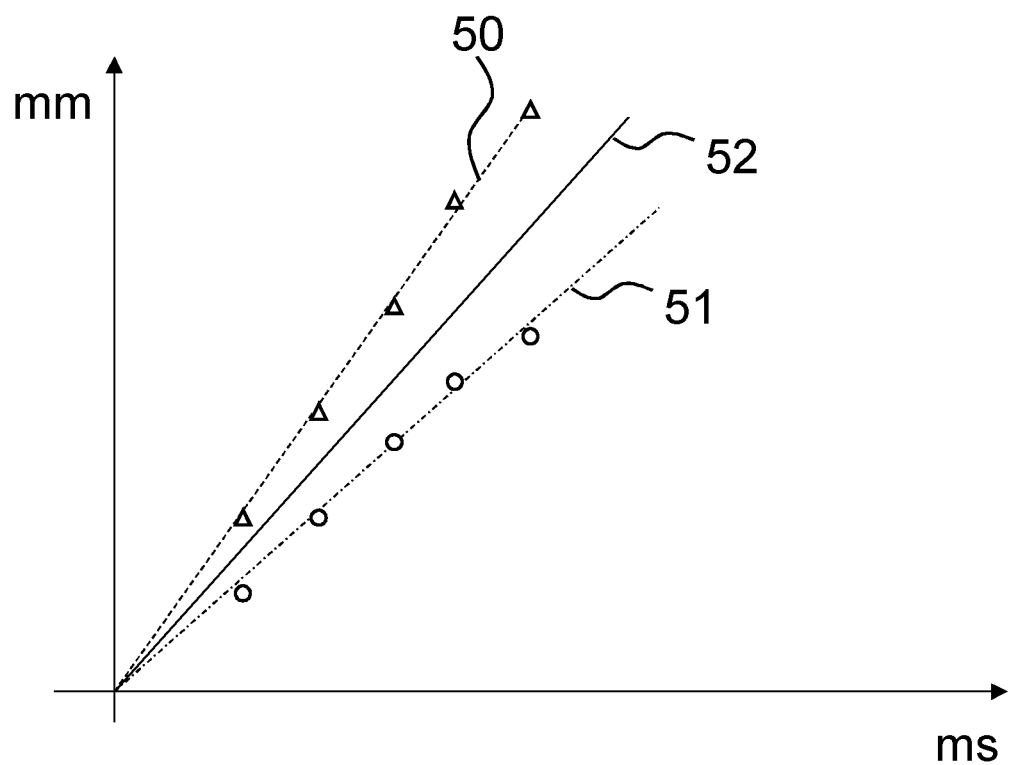
FIG. 2 is the speed curves relating to the two excitation points if the probe or the patient moves by making a rotation on the image plane.

FIG. 2 shows a case where, due to a movement of the probe or of the patient such to describe a rotation on the image plane, the speeds detected by the measurements related to the two excitation points 1 and are different from each other. This is obviously valid for movements of the probe and/or of the patient of a small entity and always with the same direction during the examination comprising the excitation both at point 1 and at point 4.

On the graph of FIG. 2, the abscissa shows the propagation time and the ordinate the space, that is the position of the lines of sight. For each line of sight the maximum of the mean displacement along the line of sight, that corresponds to the wave peak, is identified and drawn in the graph.

The values measured with reference to the first excitation point 1 are shown by small triangles, and they define a straight line whose slope corresponds the speed 50 of the shear wave 11 related to the first excitation point 1. Likewise, the values measured with reference to the second excitation point 4 are shown by small circles, and they define the speed 51 of the shear wave related to the second excitation point 4.

The movement of the probe and/or patient has caused a wrong measurement of the speed. In the case of speed 50, the movement has led to the measurement of a value higher than the real speed value, denoted by the straight line 52.

Since the movement of the probe and/or patient is always in the same direction, and since the two excitation points 1 and 4 are placed on the opposite sides of the region of interest 2, the shear waves pass through the region of interest 2 in opposite directions, and the measurements about the two excitation points 1 and 4 therefore lead to wrong speed values, one by excess and the other by defect.

Due to such reason, in this case the speed 51 detected for the second excitation point 4 has a value lower than the real speed 52, where the speed is the change in the position of the peak of the wave over time.

The real speed 52 will substantially correspond to the mean between the first speed 50 and the second speed 51.

On the basis of the detected speeds 50 and 51 therefore a mean stiffness value of the tissues in the region of interest 2 is calculated, and such calculation is performed on the basis of the mean between the speed 50 of the shear wear measured for the first excitation point 1 and the speed 51 of the shear wave measured for the second excitation point 4.

Since the measurement is performed easily only line of sight by line of sight, and therefore a shock acoustic disturbance of the first or second excitation point 1 or 4 is necessary for each one of the measurements on the different lines of sight, the examination is structured on repeated acquisition sequences.

Each sequence 6 comprises an acoustic disturbance of the first or second excitation point 1 or 4 and a measurement of the displacement on a single line of sight.

Figure 3:
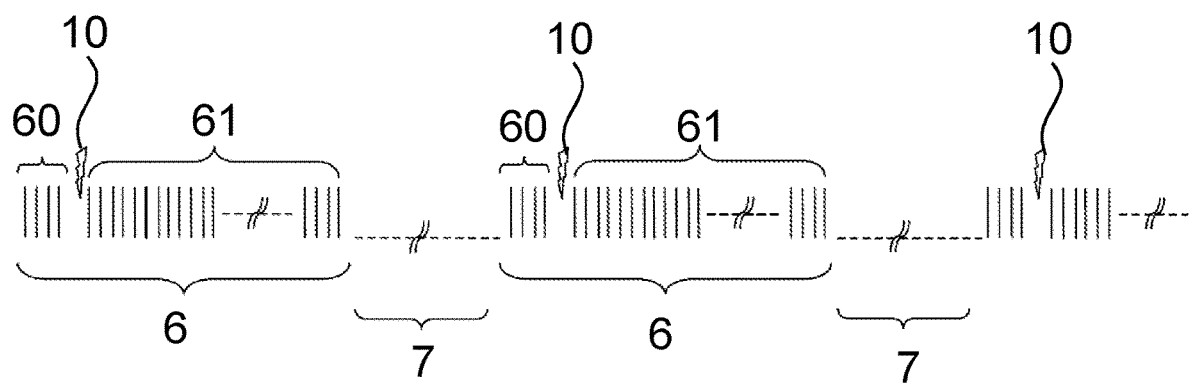
FIG. 3 is the acquisition mode.

Such as shown in FIG. 3 the sequence 6 is divided into 3 consecutive phases, plus a final pause 7.

The first phase 60 (reference) provides one or more reference measurements on the line of sight under examination. Once the line of sight under examination belonging to the region of interest 2 is identified, a given number of repetitions thereof is acquired, in a kind of short M-mode. Such acquisition then is used as reference for the comparative analysis with the further acquisitions made after the shock insonification.

The second phase 10 (shock) provides a particular, or shock, insonification corresponding to what shown in FIG. 1, in order to acoustically disturb the tissues and to follow their displacements in the subsequent third measurement phase. The pulse train corresponding to the shock acoustic disturbance for example can have a duration of 200 µs.

Due to the shock disturbance, the tissues in the surroundings of the excitation point will be displaced due to the non-linearity to the acoustic disturbance. However once the shock insonification ends they tend to go back in their natural position thus generating the shear wave, that propagates perpendicularly to the insonification front.

The third phase 61 (tracking) therefore provides to monitor the same line of sight under examination by using again an acquisition of the M-mode type, but for a considerably longer time, for example 20 ms.

Once the third phase 61 ends it is necessary to wait for a period of time before starting again with a first phase 60 on the following line of sight. Such time is necessary both for the hardware in order to be ready for a new acoustic shock disturbance and for cooling the probe and tissues.

Figure 6:
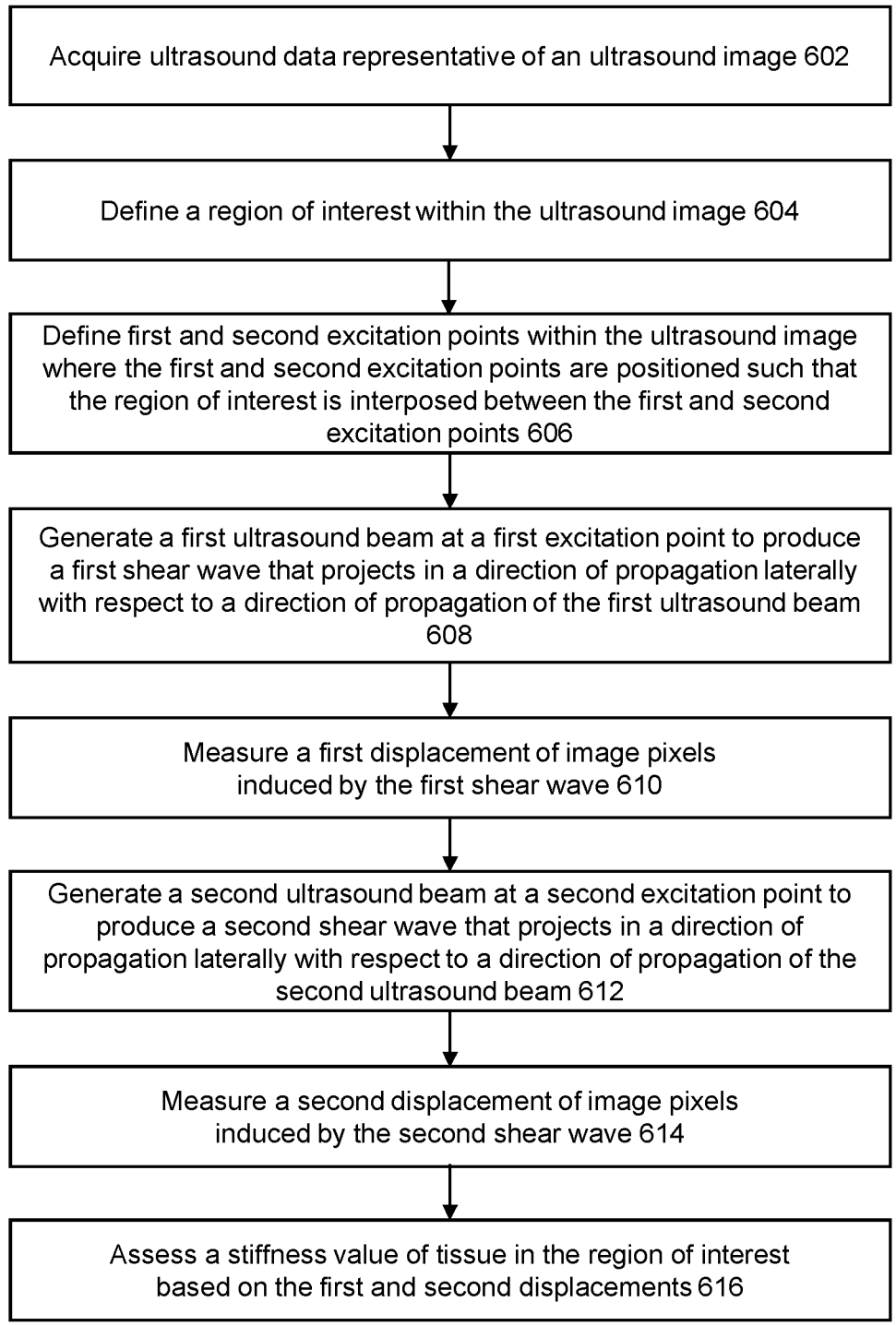
FIGS. 6-8 and 8a illustrate methods according to various embodiments.
Figure 6A:
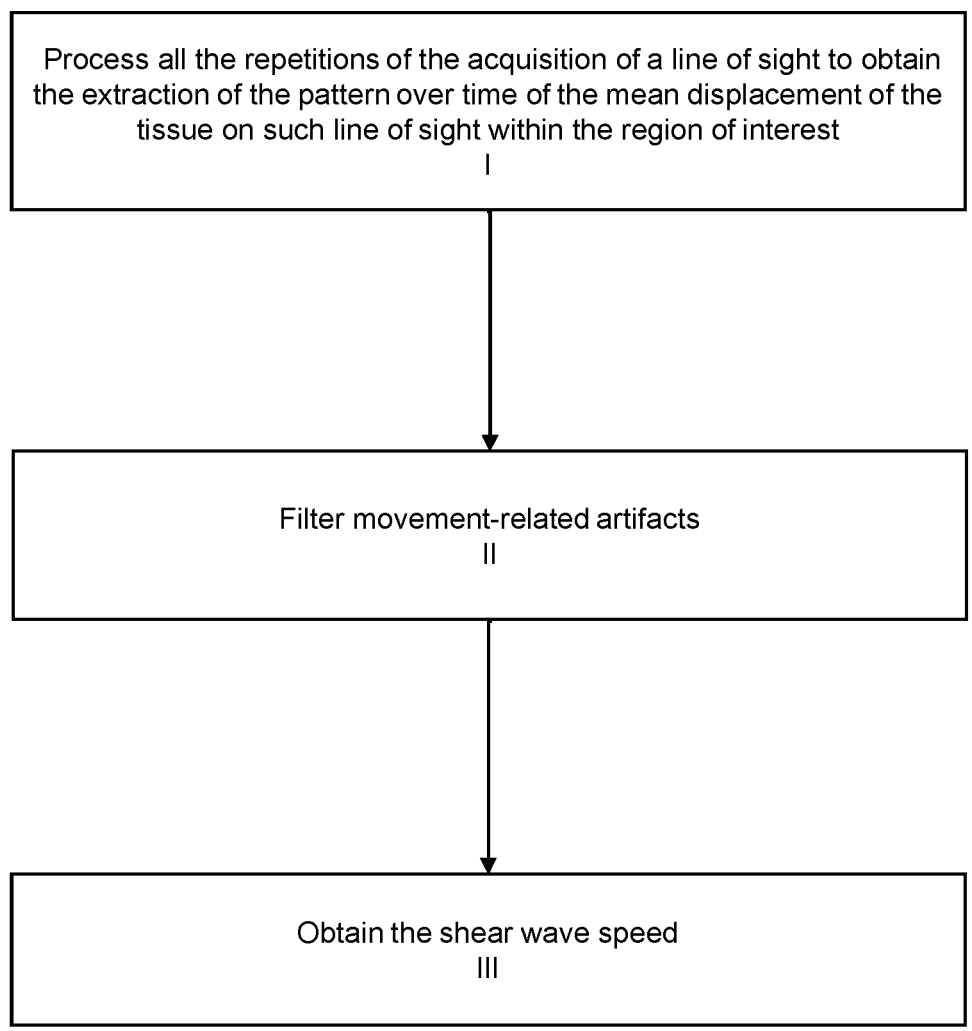

The processing of the acquired data substantially is divided in the following 3 macro-steps with reference to FIG. 6*a*:

I. Processing all the repetitions of the acquisition of a line of sight to obtain the extraction of the pattern over time of the mean displacement of the tissue on such line of sight within the region of interest 2;

II. Processing the results of the previous step, that is of the whole set of displacements belonging to a line of sight, for filtering movement-related artifacts etc.;

III. Processing the whole set of results deriving from the previous steps in order to obtain the shear wave speed of the whole observation.

Figure 6B:
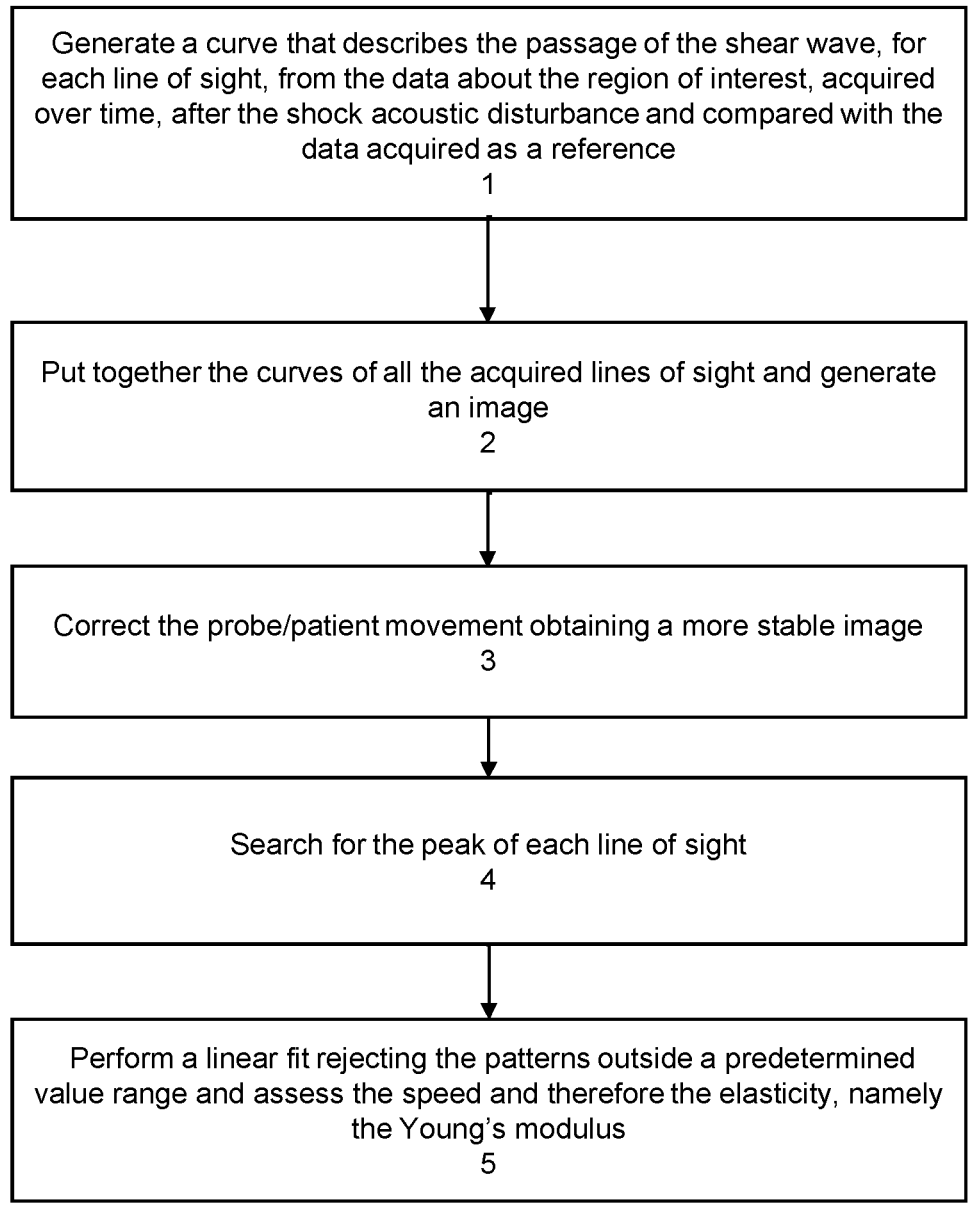

The necessary processing can be summarized as follows with reference to FIG. 6*b*:

1. for each line of sight, from the data about the region of interest 2, acquired over time, after the shock acoustic disturbance 10 and compared with the data acquired as a reference, a curve is obtained that describes the passage of the shear wave. To this end an algorithm is used for searching the zero of the complex cross-correlation phase, among not oversampled measurement and reference signals I and Q, as better explained below.

2. the curves of all the acquired lines of sight are put together and an image is generated, which is still affected by movement-related artifacts.

3. the probe/patient movement is corrected, obtaining a more stable image.

4. the search for the peak of each line of sight is carried out.

5. a linear fit is performed rejecting the patterns outside a predetermined value range and the assessment of the speed and therefore of the elasticity is obtained, namely the Young's modulus.

For the fit it is possible to use for example a "RANSAC" algorithm (RANdom Sample Consensus).

After the measurement the machine waits for a time period necessary to cool the probe and the examined tissue.

Figure 4:
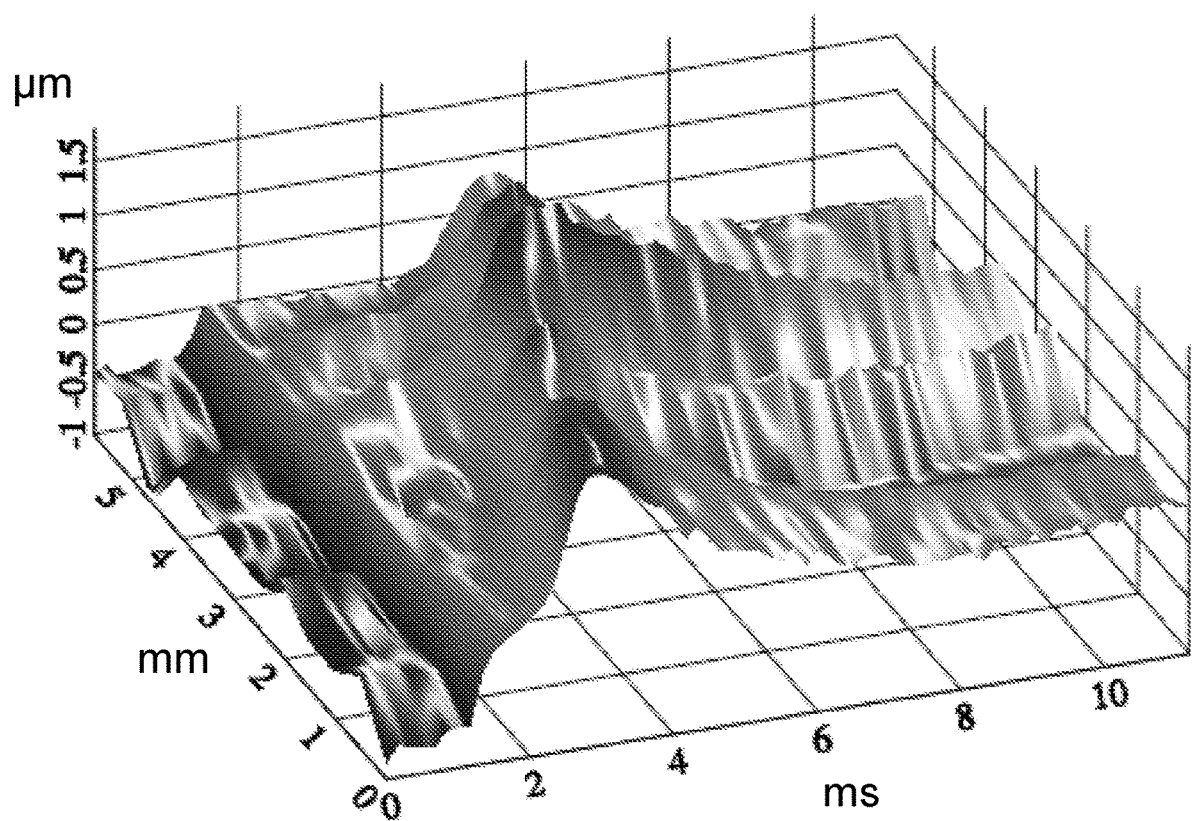
FIG. 4 is a rendering of the wave measured along the different lines of sight, without filtering the artifacts.

FIG. 4 shows an example of a real acquisition carried out on a phantom. An image of the non-interpolated shear wave, still affected by movement-related artifacts is shown. The axes respectively show the displacement in µm, time in ms from the instant of shock acoustic disturbance, and the space in mm of the lines of sight, that is the distance of the lines of sight from the excitation point.

Figure 5:
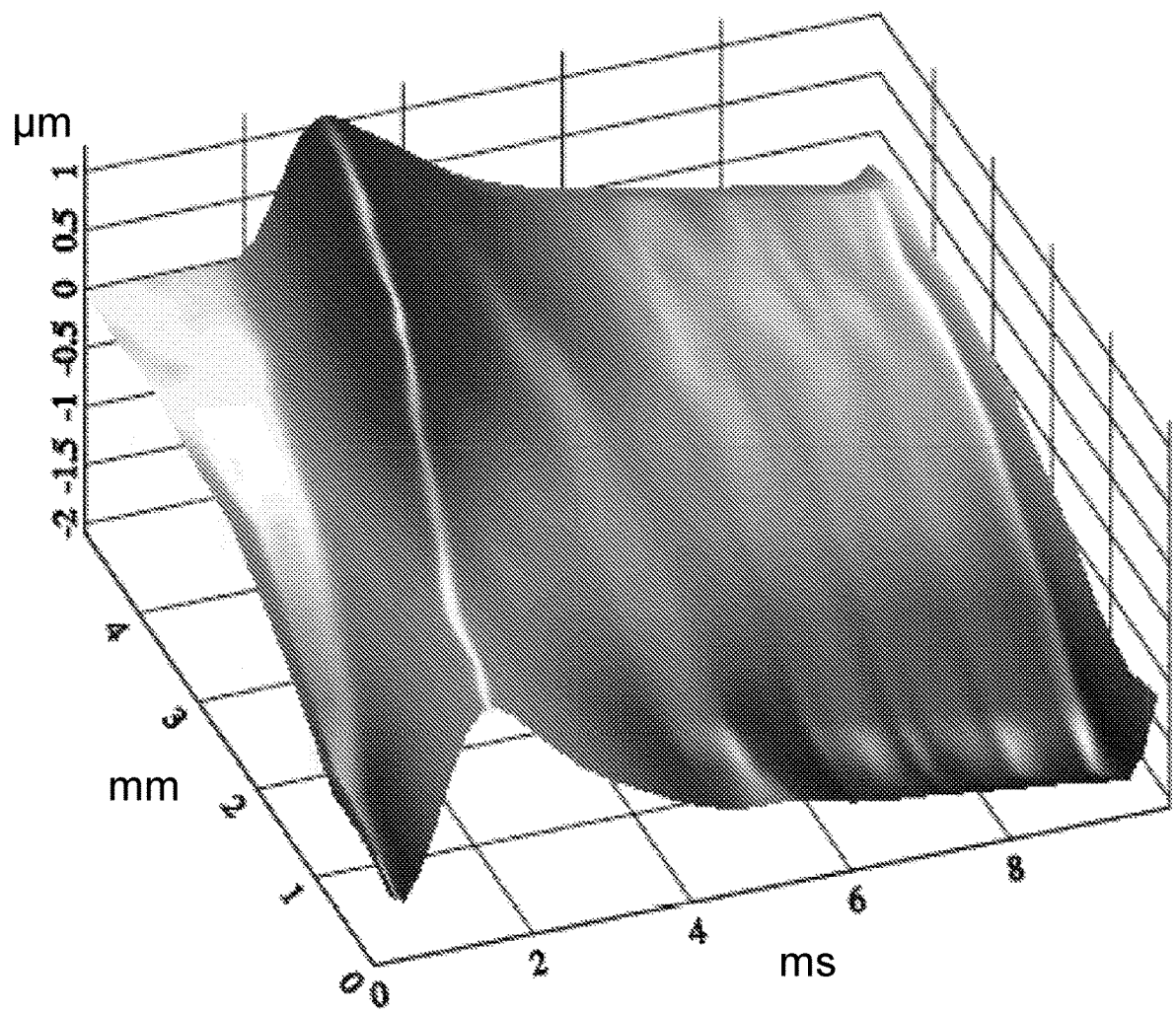
FIG. 5 is the same rendering after the filtering operation.

FIG. 5 shows the same image of the interpolated shear wave after having removed the movement-related artifacts of the longitudinal type. Longitudinal movement means the movement along the direction of propagation of the ultrasonic beams, that is the direction of the probe moving near or away from the patient.

Now the algorithm calculating the displacement of the tissue and the algorithm calculating the shear wave speed are described in detail.

Algorithm calculating the displacement.

Once the first LS (line of sight) is determined:

the Ref (reference) vectors are acquired, the shock acoustic disturbance is emitted, the Trk (tracking) measurement vectors are acquired.

Each vector is the radiofrequency (RF) signal of the current line of sight, acquired at a given instant, belonging to the selected region of interest.

For each Trk vector the displacement, over time, with respect to the Ref is searched; each displacement is distant from the previous one the time elapsing between a repetition and the following one.

The algorithm calculates the displacement of the line of sight of the current Trk with respect to the Ref one, performing the following steps:

a cluster (subset) of samples of Ref and current Trk vectors is extracted;

the clusters are windowed, for example by Hann window or tapered cosine, to make the Ref and Trk clusters similar to window edges;

the complex cross-correlation between the windowed Ref and Trk clusters is calculated (vector=[real_part, imaginary_part]=[I,Q];

the modulus and the phase of the complex cross-correlation are calculated;

the index of the maximum of the modulus of the complex cross-correlation is calculated, corresponding to a 'coarse' displacement between Ref and Trk clusters;

a range of samples of the phase (for example 3 or 5 samples) is extracted around the index of the maximum;

a 1 order fit of the phase (linear regression) is carried out;

the position of the zero of the linear regression line is calculated: such position is intermediate between 2 samples and it corresponds to a 'fine' displacement between Ref and Trk clusters;

the 'coarse' displacement is summed to the 'fine' displacement, in samples;

by knowing the sampling frequency (typically 50 MHz) the displacement is converted from sample units to µm.

Therefore the displacement of the Trk vector has been calculated with respect to the Ref vector at the first measurement instant.

Then we pass to the following cluster, partially overlapping the previous one, calculating the second point (that is distant a time equal to 1/PFR of repetitions of Trk, typically PRF=6 KHz) and so on till ending the dimension of Ref and Trk vectors.

Therefore we go on with the second line of sight, up to the last one, obtaining a plurality of displacement curves, one for each line of sight.

Algorithm calculating the shear wave speed.

From the algorithm calculating the displacement a matrix is obtained, whose rows are composed of the displacement curves.

To such matrix a moving mean filter is applied for each row, of the type [1 2 2 2 1] to reduce the noise and by a fine interpolation for example by an oversampling factor equal to 50.

Now it is possible to have spurious slopes between displacement curves of a line of sight and the other one; the origin of such phenomenon is explained by the fact that the probe or the patient or both of them can move in the longitudinal direction.

The hypothesis of a displacement during the acquisition time translates into a slope added to the curve, which is possible to be removed.

Different algorithms have been developed for removing such spurious slope:
- filtering by a band-pass filter (the movement is a low frequency, the high frequencies are noise): it has the advantage of rejecting also frequencies for example due to the movement induced by the heartbeat;
- carrying out a linear fit on the displacement curve of single LS with RANSAC algorithm, such not to consider the peak in the fit;
- carrying out a linear fit with RANSAC algorithm on the difference between neighbour displacement curves (the curves of two adjacent LS are similar, only the straight line of the displacement induced by the probe/sample substantially remains), by aligning the several LS with the first one;
- as the previous step but by aligning the curves of the several LS with the mean of the curves of LS.

Figure 3A:
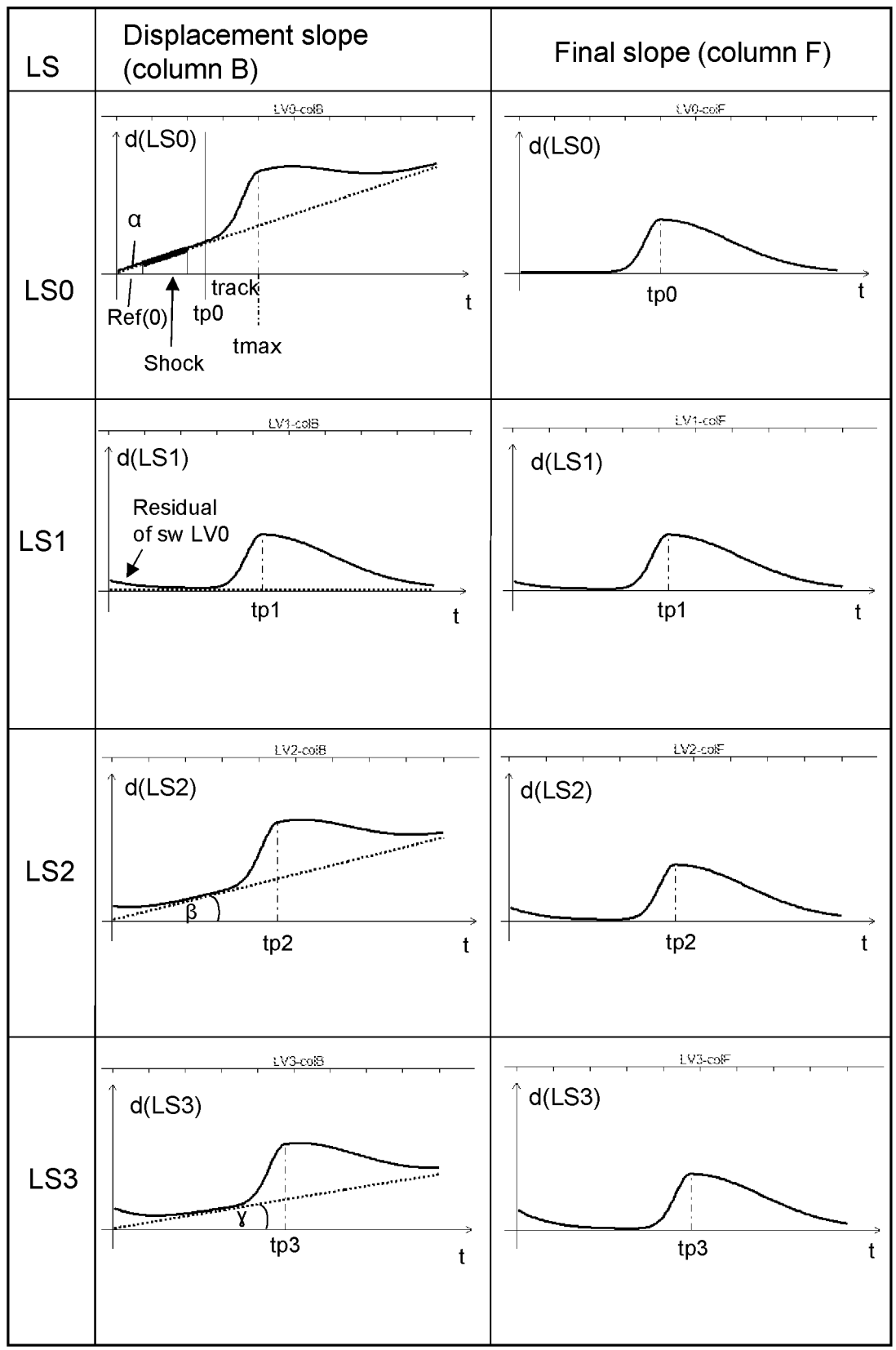
FIGS. 3a and 3b show examples of the operations on the displacement curves to correct longitudinal movement.
Figure 3B:
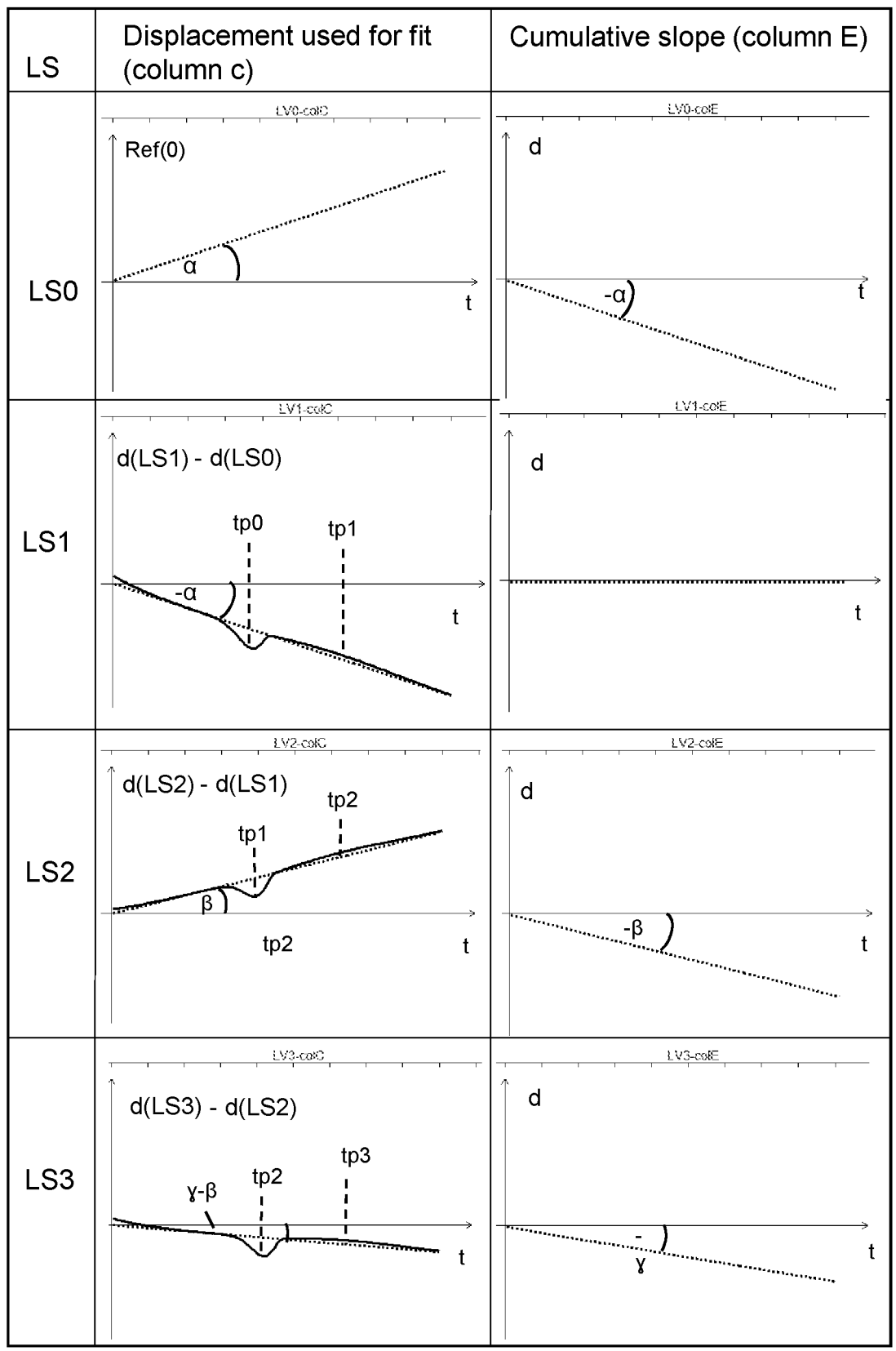
Figure 3C:
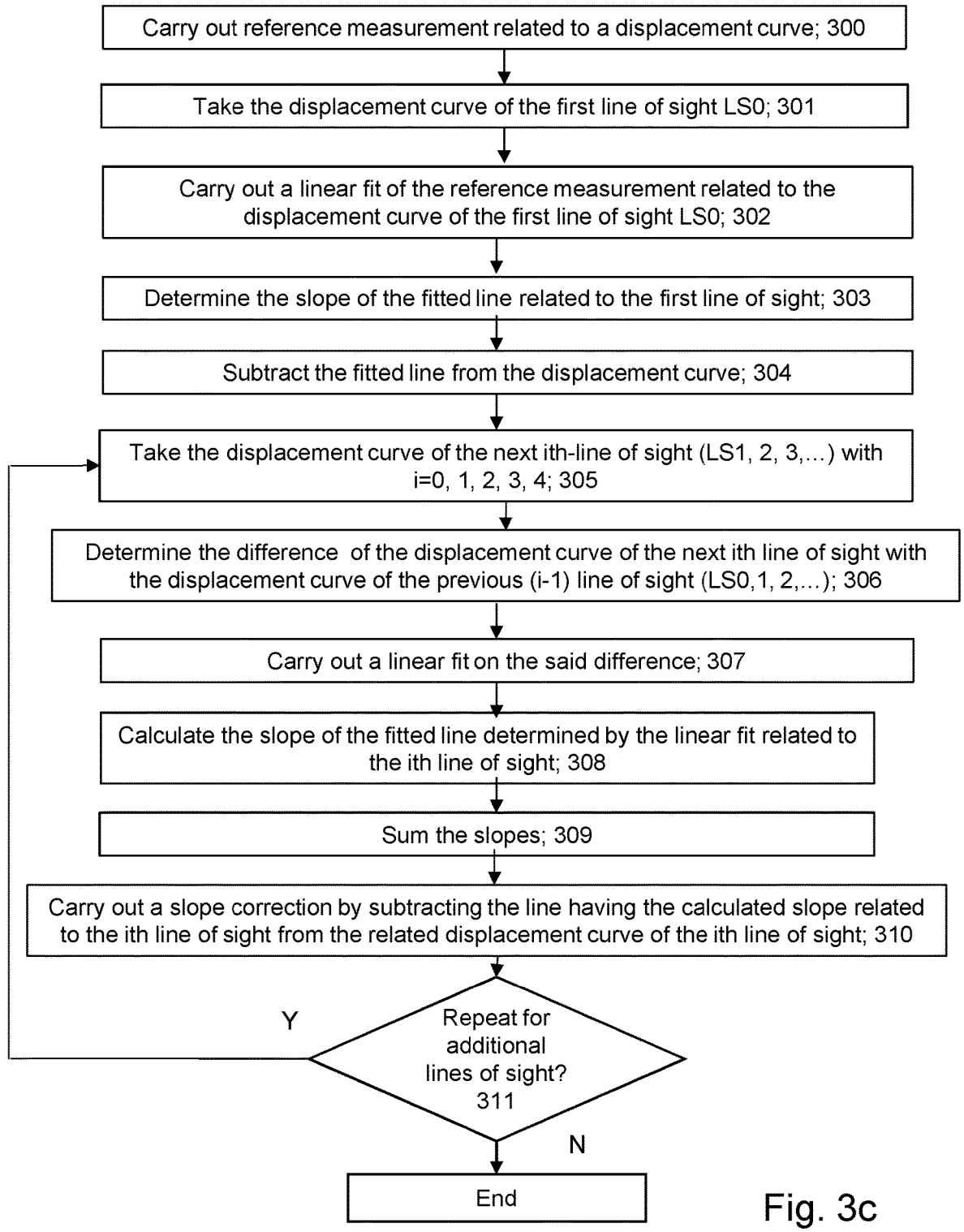
FIG. 3c shows a diagram of a method according to an embodiment for correcting spurious slopes of the displacement curves due to longitudinal movements.

With reference to FIGS. 3a, 3b and 3c, a further embodiment for removing such spurious slope provides the steps of making a linear fit of some Reference measurements related to the displacement curve of the first LS (LSO) (steps 300, 301 and 302 of FIG. 3c) and determine the slope of the fitted line (see the below table, line LSO, column C and D; step 303); and then subtract the fitted line from the displacement curve (F): Step 304 of FIG. 3c.

For the other lines of sights LS (1, 2, 3 . . . ), the embodiment provides to make a linear fit, for example using the RANSAC algorithm, on the difference between each displacement curve and the previous one (C), steps 305, 306 and 307 of FIG. 3c and calculate the slope of the fitted line (D), step 308, to be summed to the slopes found in the previous steps (E) step 309; make a slope correction by subtracting the line having the calculated slope from the related displacement curve (F) step 310.

The steps 305 to 310 are repeated for each one of the further displacement curves related to other further lines of sight, step 311.

The result is a displacement curve, for each line of sight LS, corrected from longitudinal movements, i.e. without a superimposed ramp, for which it is more reliable to calculate the temporal position of the peak.

This algorithm, working on linear fit of differences, has the advantage of not being affected by possible residual displacements due to shear-waves generated for the preceding line of sights LS thus allowing to make temporally close acquisitions related to subsequent LS.

| A<br>LS | B<br>Displacement slope | C<br>Displacement used for fit | D<br>Computed slope | E<br>Cumulative slope correction (−1*sum of computed slopes) | F<br>final slope |
|---|---|---|---|---|---|
| LS0 | α | Ref(0) | α | −α | α − α = 0 |
| LS1 | 0 | d(LS1) − d(LS0) | −α | 0 | 0 |
| LS2 | β | d(LS2) − d(LS1) | β | −β | β − β = 0 |
| LS3 | γ | d(LS3) − d(LS2) | γ − β | −γ | γ − γ = 0 |

A stabilized matrix, also for longitudinal movements, is now available.

For each LS the distance from the excitation point and the mean position of the region of interest corresponding to such line of sight (lateral distance) is calculated, by assuming the propagation of the propagation wave as a spherical wave or a cylindrical wave, and a point [X,Y]=(lateral distance, maximum instant) is defined, where maximum instant is the time corresponding to the maximum of the curve corresponding to the displacement over time, by associating the instant of the passage of the shear wave to the maximum of the displacement of the samples with respect to the reference position, as logically expected.

Therefore the points [X,Y] for all the LS are drawn in the graph and a fit with RANSAC algorithm is carried out, by eliminating the acquisitions that are too much distant from the other ones.

From the slope of the straight line the shear wave speed and consequently the Young's modulus are obtained, by assuming the tissue density as a unit quantity.

FIGS. 3c, discussed above, 6-8 and 8a illustrate methods for quantifying the elasticity of biologic tissues by ultrasound in accordance with embodiments herein. The operations of FIGS. 3c, 6-8 and 8a may be carried out by one or more processors of an ultrasound system in response to execution of program instructions stored in the memory of the ultrasound system. The operations of FIGS. 3c, 6-8 and 8a may be carried out by one or more digital signal processors (DSPs), field programmable gate arrays (FPGAs) and/or other hardware or firmware components. Additionally or alternatively, the operations of FIGS. 3c, 6-8 and 8a may be carried out by the processors within one or more servers, on a network, in response to execution of program instructions stored at the server, and/or other applications stored at the server.

At 602 an ultrasound probe acquires ultrasound data representative of an ultrasound image. For example, one or more processors, beamformers and other hardware and software manage transmission and reception of ultrasound signals to acquire ultrasound echo signals representative of at least a portion of a patient (e.g., human or animal). At 604 a processor defines a region of interest within the ultrasound image. For example, the region of interest may be automatically defined based on automated identification of landmarks or marks in the ultrasound image.

Alternatively or additionally, the region of interest may be defined by a user of the ultrasound system. For example, one or more initial images (e.g., B-mode, Color Doppler, etc.) are presented on a display and the user utilizes the user interface to designate the region of interest. The region of interest may be designated in various manners, such as by designating one or more points within the examination region, designating one or more boundaries within the examination region and the like.

The region of interest includes lateral side boundaries along opposite sides of the ROI. The side boundaries project from the surface of the transducers of the ultrasound probe. The ROI also includes top and bottom boundaries that extend from side to side in directions generally common with the surface of the transducers of the ultrasound probe. As non-limiting examples, the top and bottom boundaries may extend parallel to one another or along common concentric arcs.

At 606 the processor defines first and second excitation points within the ultrasound image where the first and second excitation points are positioned such that the region of interest is interposed between the first and second excitation points. For example, the processor may establish positions of the first and second excitation points by defining a reference distance/depth from the surface of the transducers of the probe and a reference lateral spacing. The reference depth and laterally spacing may be predetermined distances from corresponding top, bottom and/or side boundaries of the ROI. The reference depth may be a predetermined depth from the probe. The reference depth may be set to align with a feature of interest in the ROI. For example, the user may designate an area of tissue for which elasticity is of interest. The processor may then set the reference depth to align with tissue area for which elasticity is to be measured. Optionally, the reference depth may be positioned dynamically based on other factors. For example, the reference depth may be set to correspond to a center depth of the ROI or may be set at another depth relative to the top and bottom boundaries of the ROI (e.g., in upper third, middle third, lower third).

At 608 the processor generates a first ultrasound beam (also referred to as a first acoustic disturbance ultrasound beam) at the first excitation point to produce a first shear wave that projects in a direction of propagation laterally with respect to a direction of propagation of the first ultrasound beam. The shear wave is illustrated in FIG. 1 at reference numeral 11. The lateral direction may extend parallel to the surface of the transducers of the ultrasound probe. Additionally or alternatively, the lateral direction may extend at an acute with respect to the surface of the transducers of the ultrasound probe. The lateral direction generally extends through the ROI.

At 610 the processor measures a first displacement of image pixels induced by the first shear wave. The operations of 610 are described below in more detail in connection with FIGS. 7 and 8.

At 612 the processor generates a second ultrasound beam (also referred to as a second acoustic disturbance ultrasound beam) at a second excitation point to produce a second shear wave that projects in a direction of propagation laterally with respect to a direction of propagation of the second ultrasound beam. The direction of propagation of the second shear wave may be parallel or non-parallel with the direction of propagation of the first shear wave. While the first and second shear waves projection in multiple directions from the corresponding excitation points, the directions of propagation of the first and second ultrasound beams at least partially extends toward one another.

At 614 the processor measures a second displacement of image pixels induced by the second shear wave. The operations of 614 are described below in more detail in connection with FIGS. 7 and 8.

At 616 the processor assesses a stiffness value of tissue in the region of interest based on the first and second displacements. Optionally, the stiffness value of the tissue may be calculated based on reference measurements.

Figure 7:
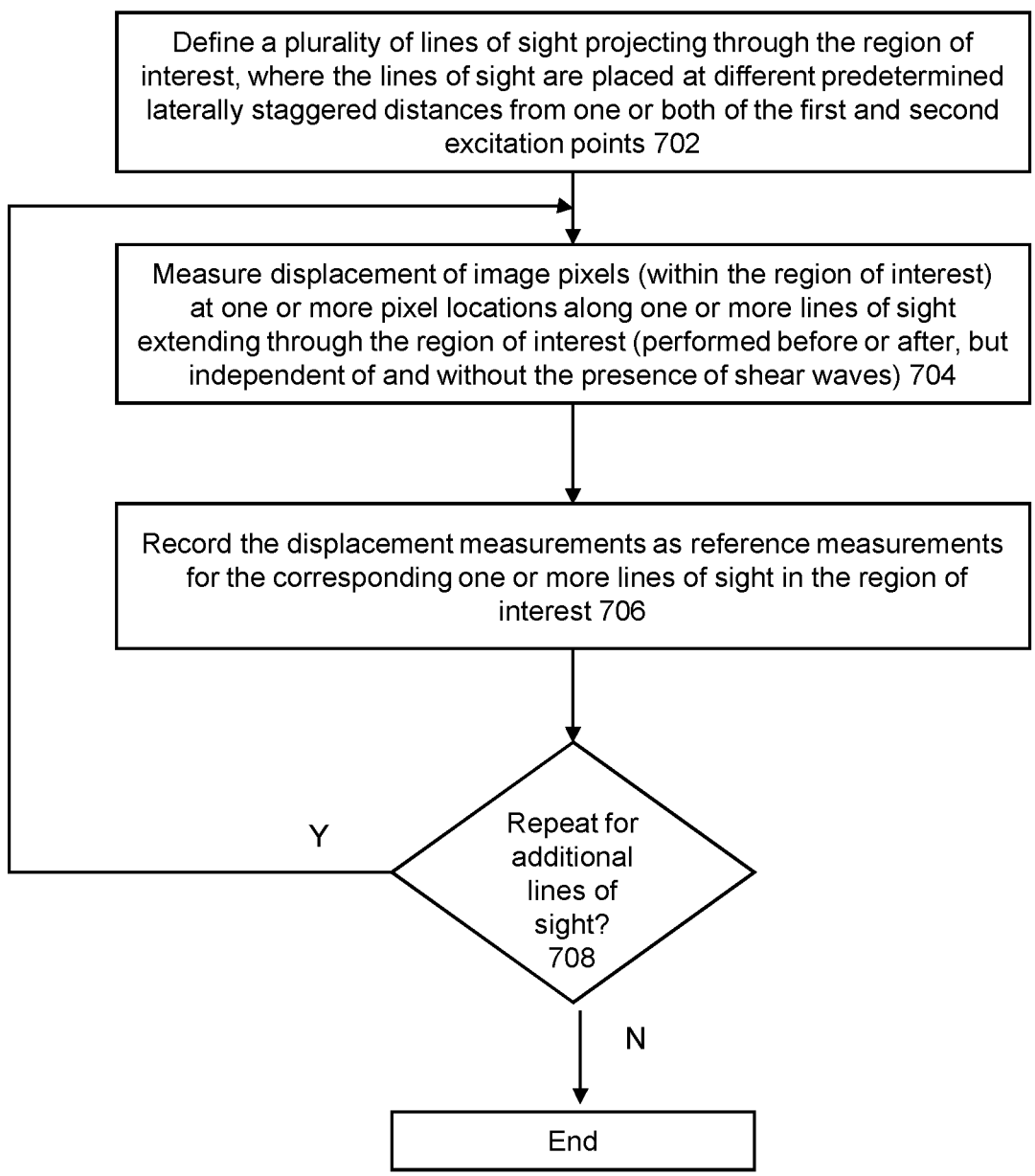

FIG. 7 illustrates a process for determining reference measurements in the ROI in connection with lines of sight in accordance with embodiments herein. At 702 the processor defines a plurality of lines of sight projecting through the region of interest. The lines of sight may be placed at different positions within the ROI. For example, the lines of sight may be positioned at different predetermined laterally staggered distances from one or both of the first and second excitation points. For example, the lines of sight may be evenly distributed laterally across the ROI.

At 704 the processor measures displacement of image pixels (within the region of interest) at one or more pixel locations along one or more lines of sight extending through the region of interest. The displacement measurements are performed before or after, but independent of and without the presence of shear waves. For example, a set of pixel locations may be defined along each line of sight where the pixel locations are evenly distributed along the line of sight. Optionally, the pixel locations may be located proximate to a feature of interest in the ROI. The pixel locations may be located at the same locations or at different locations along each of the lines of sight.

At 706 the processor records the displacement measurements as reference measurements for the corresponding one or more lines of sight in the region of interest. At 708, the processor determines whether to repeat the process for additional lines of sight.

If so, flow returns to 704 and additional reference measurements are obtained for the same or different lines of sight. If not, the process of FIG. 7 ends. The process of FIG. 7 collects reference measurements at the pixel locations. The reference measurements may be collected at some, but not all, of the pixel locations for which subsequent measurements are to be collected.

Figure 8:
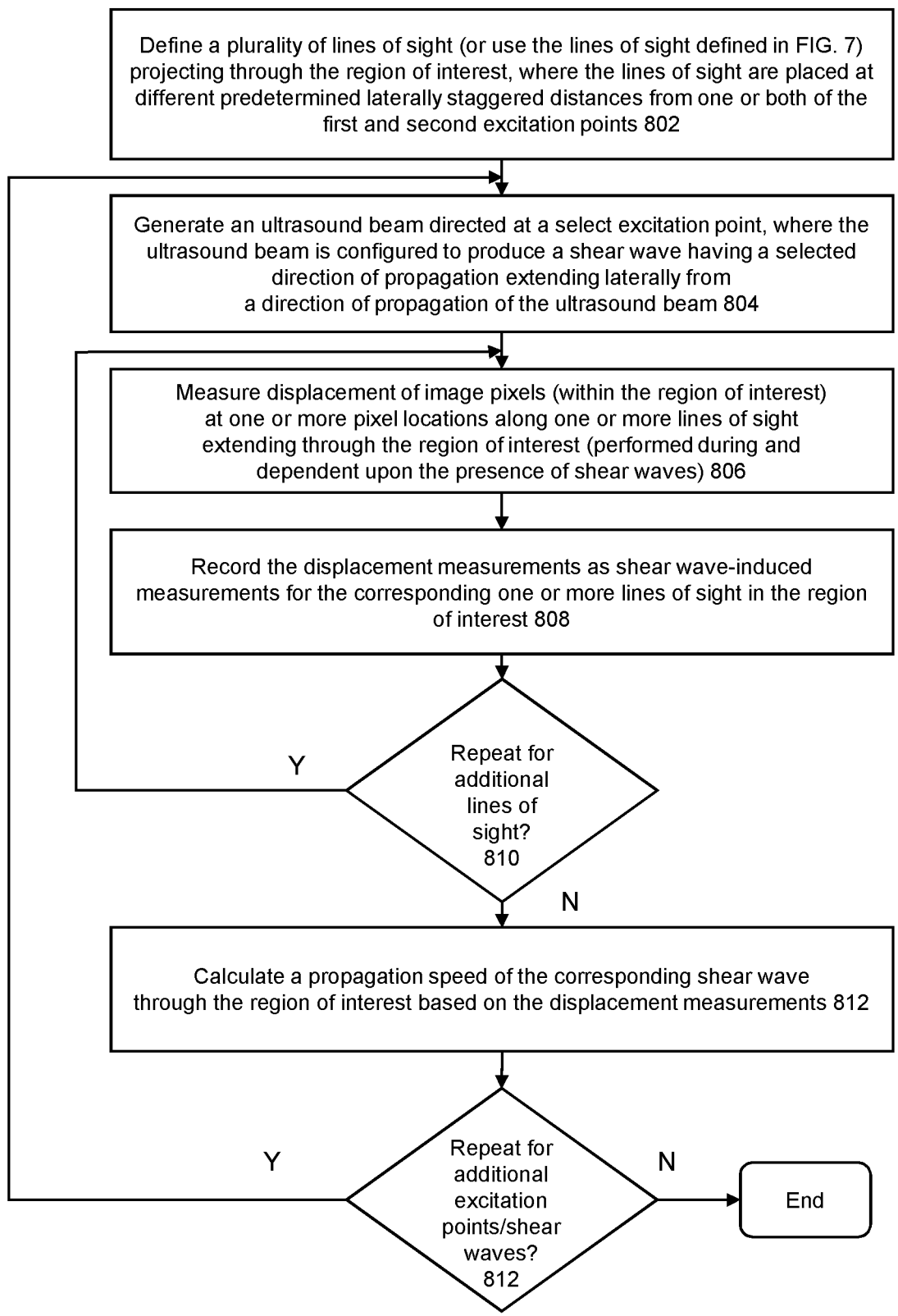

FIG. 8 illustrates a process for measuring displacement induced by shear waves in accordance with embodiments herein. The operations of FIG. 8 are performed in connection with the operations of 608 to 616 in FIG. 6.

At 802 the processor defines a plurality of lines of sight (or use the lines of sight defined in FIG. 7) projecting through the region of interest, where the lines of sight are placed at different predetermined laterally staggered distances from one or both of the first and second excitation points. The lines of sight may be the same as or different from the lines of sight utilized to collect the reference measurements of FIG. 7.

At 804 the processor generates an ultrasound beam directed at a select excitation point, where the ultrasound beam is configured to produce a shear wave having a select direction of propagation extending laterally from a direction of propagation of the ultrasound beam. As explained herein, the direction of propagation of the shear wave may be perpendicular or oriented at an acute angle to the direction of propagation of the ultrasound beam.

At 806 the processor measures displacement of image pixels (within the region of interest) at one or more pixel locations along one or more lines of sight extending through the region of interest. The displacement measurements are performed during the presence of shear waves such that the displacement is effected by and dependent upon the shear waves, and thus the measurements represent shear wave induced displacement measurements. Optionally, the displacement measurements may be adjusted based on the reference measurements to remove non-shear wave components. For example, when a reference measurement (as collected in connection with FIG. 7) indicates that a select pixel location exhibits a baseline amount of movement, the baseline amount of movement may be subtracted, as a non-shear wave component, from the displacement measurement in the presence of shear waves. Optionally, the shear wave induced displacement measurements may be adjusted in other manners based on the reference measurements. For example, the shear wave induced displacement measurements may be filtered based on, averaged with or otherwise combined with the reference displacement measurements. Alternatively, the shear wave induced displacement measurements may not be adjusted in any manner for non-shear wave induced components.

At 808 the processor records the displacement measurements as shear wave-induced measurements for the corresponding one or more lines of sight in the region of interest.

At 810, the processor determines whether to collect displacement measurements for additional lines of sight. If so, flow returns to 806. Otherwise, flow continues to 812. The process of 806 and 808 is repeated for a select number of lines of sight.

At 812 the processor calculates a propagation speed of the corresponding shear wave through the region of interest based on the displacement measurements.

At 814, the processor determines whether to repeat the displacement measurements for additional excitation points and additional shear waves. If so, flow returns to 804. Otherwise, the process of FIG. 8 ends. It is understood that the operations of FIG. 8 may be repeated only once or multiple times in connection with each of the first and second excitation points.

Figure 8A:
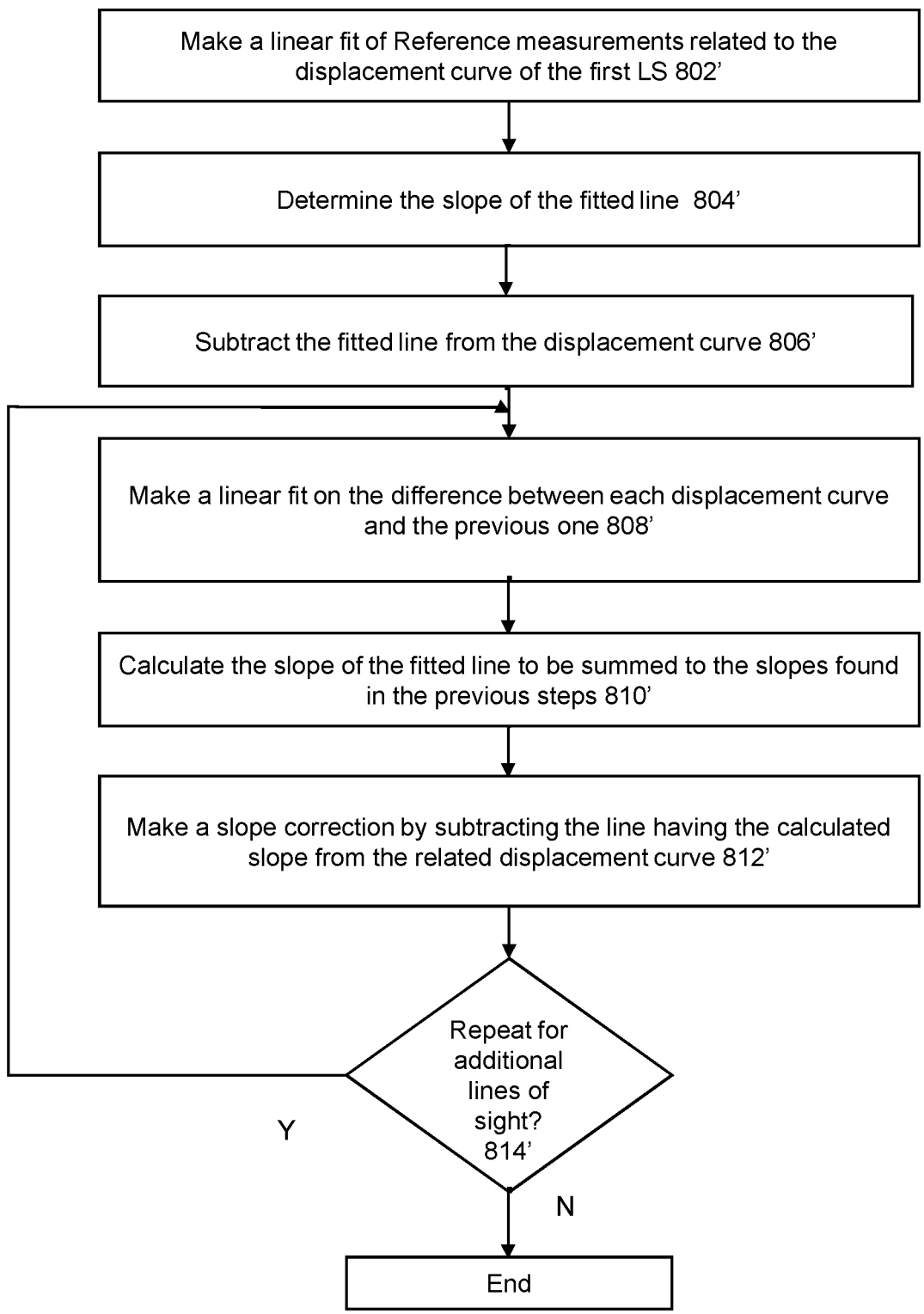

FIG. 8a illustrates a process for correction of longitudinal displacement in accordance with embodiments herein.

At 802', the processor makes a linear fit of Reference measurements related to the displacement curve of the first LS 802'.

At 804', the processor determines the slope of the fitted line.

At 806' the processor subtracts the fitted line from the displacement curve.

Now the processor start working on the subsequent lines of sight. At 808', the processor makes a linear fit on the difference between each displacement curve and the previous one.

At 810', the processor calculates the slope of the fitted line to be summed to the slopes found in the previous steps.

At 812' the processor makes a slope correction by subtracting the line having the calculated slope from the related displacement curve.

At 814', the processor determines whether to repeat the slope correction for lines of sights. If so, flow returns to 808'. Otherwise, the process of FIG. 8a ends.

Figure 9:
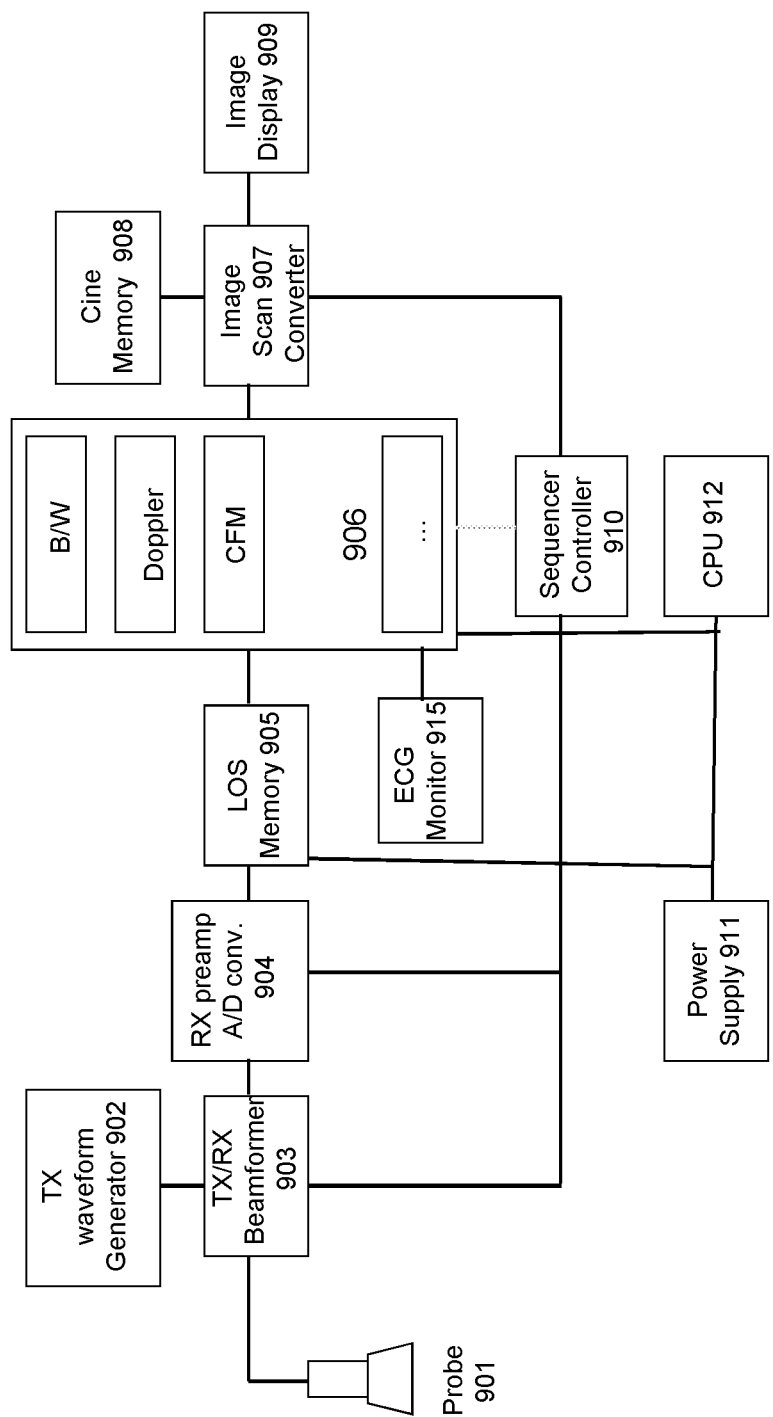
FIG. 9 illustrates a block diagram of the system according to an embodiment.

FIG. 9 illustrates a high-level block diagram of a ultrasound system. Portions of the system (as defined by various functional blocks) may be implemented with dedicated hardware, such as transmit/receive (TX/RX) driving/preamp and power switching circuitry, which may utilize analog components. Digital components, DSPs and/or FPGAs, may be utilized to implement the sequencer controller and the timing generator.

The ultrasound system of FIG. 9 includes one or more ultrasound probes 901. The probe 901 may include various transducer array configurations, such as a one dimensional array, a two dimensional array, a linear array, a convex array and the like. The transducers of the array may be managed to operate as a 1D array, 1.25D array, 1.5D array, 1.75D array, 2D array, 3D array, 4D array, etc.

The ultrasound probe 901 is coupled over a wired or wireless link to a beamformer 903. The beamformer 903 includes a transmit (TX) beamformer and a receive (RX) beamformer that are jointly represented by TX/RX beamformer 903. The beamformer 903 supplies transmit signals to the probe 901 and performs beamforming of "echo" signals that are received by the probe 901.

A TX waveform generator 902 is coupled to the beamformer 903 and generates the transmit signals that are supplied from the beamformer 903 to the probe 901. The transmit signals may represent various types of ultrasound TX signals such as used in connection with B-mode imaging, color Doppler imaging, pulse-inversion transmit techniques, contrast-based imaging, M-mode imaging and the like. In accordance with embodiments herein, the transmit signals include acoustic disturbance ultrasound (ACU) beam (10, 10' in FIG. 1) that are directed at select excitation points. The ACU beams are configured to generate shear waves as described herein.

The beamformer 903 performs beamforming upon received echo signals to form beamformed echo signals in connection pixel locations distributed across the region of interest. For example, in accordance with certain embodiments, the transducer elements generates raw analog receive signals that are supplied to the beamformer. The beamformer adjusts the delays to focus the receive signal along a select receive beam and at a select depth within the ROI. The beamformer adjusts the weighting of the receive signals to obtain a desired apodization and profile. The beamformer sums the delayed, weighted receive signals to form RF beamformed signals. The RF beamformed signals are digitized at a select sampling rate by the RX preamp and A/D converter 904. The RF beamformed signals are converted to I,Q data pairs.

The TX waveform generator 902, TX/RX beamformer 903 and A/D converter 904 cooperate to generate first and second acoustic disturbance ultrasound beams (10, 10') directed at first and second excitation points (1, 4). The first and second acoustic disturbance ultrasound beams are configured to produce first and second shear waves (11, 11') that have directions of propagation extending laterally from the directions of propagation of the first and second acoustic disturbance ultrasound beams (10, 10'). The I,Q data pairs are saved as image pixels in the line of sight (LOS) memory. For example, the LOS memory may include LOS memory portions associated with each line of sight through the ROI. The I,Q data pairs, defining the image pixels for corresponding individual ROI locations along a corresponding LOS, are saved in the correspond LOS memory portion. A collection of image pixels (e.g., I,Q data pairs) are collected over time and saved in the LOS memory 905. The image pixels correspond to tissue and other anatomy within the ROI. As the ROI experiences the shear waves, the tissue and other anatomy in the ROI moves in response to the shear waves. The collection of image pixels capture the movement of tissue other anatomy within the ROI.

In embodiments, a dedicated sequencer/timing controller 910 may be programmed to manage acquisition timing which can be generalized as a sequence of firings aimed to locally generate shear waves aside the measurement box followed by tracking firings to monitor transition of the shear waves through the acquisition lines (LOS) in the measurement box (corresponding to the ROI). Optionally, idle phases can be added to control heating of the probe and manage compliance with safety emission regulations.

A sequence controller 910 manages operation of the TX/RX beamformer 903 and the A/D converter 904 in connection with transmitting ADU beams and measuring image pixels at individual LOS locations along the lines of sight. The sequence controller 910 manages collection of reference measurements and shear-wave induced measurements. The sequence controller 910 provides a pause period between a last measurement along one line of sight and a first measurement along a following line of sight.

One or more processors 906 perform various processing operations as described herein. The CPU 912 may perform one or more of the operations described herein in connection with generation of shear waves, measurement of displacement, calculation of displacement speed, calculation of stiffness values and the like.

Among other things, the processor 906 and/or CPU 912 analyses the image pixels to measure displacement of the image pixels. The processor 906 and/or CPU 912 measures the displacement at image pixels for the plurality of lines of sight placed in the region of interest. The lines of sight are located at different predetermined laterally staggered distances from the first and second excitation point (1), (4). The processor measures first and second displacements of the image pixels induced by the first and second shear waves (11, 11'), respectively.

The processor 906 and/or CPU 912 also calculates first and second speeds of the first (11) and second (11') shear waves, respectively, based on the displacements measured at the individual LOS locations. The processor 906 and/or CPU 912 also assesses a stiffness value based on the first and second speeds.

For example, the processor 906 and/or CPU 912 may assess the stiffness value by calculating a mean stiffness value on a basis of an average between the first and second speeds of the first and second shear wave, respectively.

As explained herein, the processor 906 and/or CPU 912 obtaining one or more reference measurements for a plurality of lines of sight in the region of interest, prior to generating the first and second shear waves. The processor 906 and/or CPU 912 measures the first and second shear waves (11, 11') includes measuring mean displacement over time of the tissue along a plurality of line of sights and identifying a peak of the mean displacements.

For example, the measurements by the processor 906 and/or CPU 912 may include calculating a cross-correlation between the measurements associated with the first and second shear waves and a reference measurement obtained independent of the first and second shear waves. The processor 906 and/or CPU 912 measures displacement over time of the tissue along a plurality of line of sights and calculates speeds of the first and second shear waves (11, 11') based, in part, on distances of the corresponding lines of sight from the first and second excitation points (1, 4).

The processor 906 and/or CPU 912 also performs conventional ultrasound operations. For example, the processor 906 executes a B/W module to generate B-mode images. The processor 906 and/or CPU 912 executes a Doppler module to generate Doppler images. The processor executes a Color flow module (CFM) to generate color flow images. The processor 906 and/or CPU 912 may implement additional ultrasound imaging and measurement operations. Optionally, the processor 906 and/or CPU 912 may filter the first and second displacements to eliminate movement-related artifacts.

An image scan converter 907 performs scan conversion on the image pixels to convert the format of the image pixels from the coordinate system of the ultrasound acquisition signal path (e.g., the beamformer, etc.) and the coordinate system of the display. For example, the scan converter 907 may convert the image pixels from polar coordinates to Cartesian coordinates for image frames.

A cine memory 908 stores a collection of image frames over time. The image frames may be stored formatted in polar coordinates, Cartesian coordinates or another coordinate system.

An image display 909 displays various ultrasound information, such as the image frames and information measured in accordance with embodiments herein. For example, the image display 909 displays the stiffness values, displacement measurements, displacement speeds, and other information calculated in accordance with embodiments herein. The stiffness values, displacement measurements, displacement speeds, and other information may be displayed as image information, as numeric values, graphical information and the like. The display 909 displays the ultrasound image with the region of interest shown. Optionally, the display 909 may display indicia indicating the first and second excitation points (1, 4), where the indicia are overlaid on the ultrasound image and/or presented along opposite sides of the ultrasound image.

Optionally, the system of FIG. 9 may include an ECG monitor 915 that couples an ECG sensor to the patient and records an ECG signal indicative of the patient's heart rate. The processor 906 and/or sequence controller 910 synchronize the generation of acoustic disturbance ultrasound beams (10, 10') and the measurement of the first and second displacements of the image pixels induced by the first and second shear waves (11, 11') with the ECG signal.

The blocks/modules illustrated in FIG. 9 can be implemented with dedicated hardware (DPSs, FPGAs, memories) and/or in software with one or more processors.

A control CPU module 912 is configured to perform various tasks such as implementing the user/interface and overall system configuration/control. In case of fully software implementation of the ultrasound signal path, the processing node usually hosts also the functions of the control CPU.

A power supply circuit 911 is provided to supply power to the various circuits, modules, processors, memory components, and the like. The power supply 911 may be an A.C. power source and/or a battery power source (e.g., in connection with portable operation).

Optionally, in point Shear Wave acquisition, the RX tracking lines (line of sights—LOSs) may be temporarily stored, either as pure RF or as I/Q data, in the front-end local memories. The processing may be implemented by a dedicated processor module 906 and/or a CPU 912. Processed data, may be formatted as shear wave speed measurements or stiffness values. These, are then added to the ancillary data of the field-of-view under scan and properly reported as an overlay to the image displayed on system's monitor.

The invention claimed is:

1. A Method for quantifying the elasticity of biologic tissues by ultrasounds, comprising the following:
 a) acquiring an ultrasound image of biologic tissue via an ultrasound probe;
 b) defining a region of interest in the image, the region of interest including image pixels;
 c) generating a first acoustic disturbance focused ultrasound beam directed at a first excitation point, the first acoustic disturbance ultrasound beam configured to produce a first shear wave that has a direction of propagation extending laterally from a direction of propagation of the first acoustic disturbance ultrasound beam;
 d) measuring a first displacement of the image pixels induced by the first shear wave;
 e) after passage of the first shear wave through the region of interest, generating a second acoustic disturbance focused ultrasound beam directed at a second excitation point, the second acoustic disturbance ultrasound beam configured to produce a second shear wave that has a direction of propagation extending laterally from a direction of propagation of the second acoustic disturbance ultrasound beam and that passes through the region of interest in a direction opposite to the first shear wave;
 defining the first and second excitation points and to be positioned such that the region of interest is interposed between the first excitation point and the second excitation point;

g) measuring a second displacement of the image pixels induced by the second shear wave; and h) assessing a stiffness value of tissue in the region of interest based on the first and second displacements measured at d) and g).

2. The method according to claim 1, further comprising:

calculating first and second speeds of the first and second shear waves, respectively, based on the displacements measured at d) and g); and assessing the stiffness value based on the first and second speeds.

3. The method according to claim 2, wherein the assessing operation includes calculating a mean stiffness value on a basis of an average between the first and second speeds of the first and second shear wave, respectively.

4. The method according to claim 1, wherein the defining operation includes defining the first and second excitation points to be positioned in such a manner that the first and second shear waves passes through the region of interest.

5. The method according to claim 1, wherein the measuring operations at d) and g) include measuring the displacement of the image pixels at a plurality of lines of sight placed in the region of interest at different predetermined laterally staggered distances from the first and second excitation point.

6. The method according to claim 1, further comprising obtaining one or more reference measurements for a plurality of lines of sight in the region of interest, prior to generating the first and second shear waves.

7. The method according to claim 1, wherein the measuring of the first and second shear waves includes measuring mean displacement over time of the tissue along a plurality of line of sights and identifying a peak of the mean displacements.

8. The method according to claim 7, wherein the measuring includes providing a pause period between a last measurement along one line of sight and a first measurement along a following line of sight.

9. The method according to claim 1, wherein the measuring operations at d) and g) include calculating a cross-correlation between the measurements associated with the first and second shear waves and a reference measurement obtained independent of the first and second shear waves.

10. The method according to claim 9, wherein the measuring operation includes measuring displacement over time of the tissue along a plurality of line of sights and calculating speeds of the first and second shear waves based, in part, on distances of the corresponding lines of sight from the first and second excitation points.

11. The method according claim 1, further comprising displaying the ultrasound image with the region of interest shown, and the first excitation point and the second excitation point being further displayed on the ultrasound image.

12. The method according claim 1, further comprising recording an ECG signal, and synchronizing the generation of acoustic disturbance ultrasound beams and the measurement of the first and second displacements of the image pixels induced by the first and second shear waves with the ECG signal.

13. The method according to claim 1, further comprising filtering the first and second displacements to eliminate movement-related artifacts.

14. The method according to claim 1, wherein the direction of propagation of the first shear wave passes through the region of interest in a direction opposite to the direction of propagation of the second shear wave through the region of interest.

15. The method according to claim 1, wherein a correction of longitudinal movement is made by subtracting from each displacement of image pixels a curve having a correction slope.

16. The method according to claim 15, wherein the correction slope is calculated by making a linear fitting between displacements related to subsequent lines of sight.

17. The method according to claim 16, wherein the correction slope for one line of sight is obtained by summing all the correction slopes calculated for the previous lines of sight, the first correction slope being calculated on a reference displacement.

18. An ultrasound system for quantifying elasticity of biologic tissue, comprising:

an ultrasound probe configured to acquire an ultrasound image;

a memory storing program instructions;

at least one processor that executes the program instructions to:

define a region of interest in the ultrasound image, the region of interest including image pixels;

generate a first acoustic disturbance focused ultrasound beam directed at a first excitation point, the first acoustic disturbance ultrasound beam configured to produce a first shear wave that has a direction of propagation extending laterally from a direction of propagation of the first acoustic disturbance ultrasound beam;

measure a first displacement of the image pixels induced by the first shear wave;

wherein the at least one processor further executes the program instructions to:

after passage of the first shear wave through the region of interest, generate a second acoustic disturbance focused ultrasound beam directed at a second excitation point, the second acoustic disturbance ultrasound beam configured to produce a second shear wave that has a direction of propagation extending laterally from a direction of propagation of the second acoustic disturbance ultrasound beam and that passes through the region of interest in a direction opposite to the first shear wave;

define the first and second excitation points to be positioned such that the region of interest is interposed between the first excitation point and the second excitation point;

measure a second displacement of the image pixels induced by the second shear wave; and assess a stiffness value of tissue in the region of interest based on the first and second displacements measured.

19. The system according to claim 18, wherein the at least one processor is further configured to:

calculate first and second speeds of the first and second shear waves, respectively, based on the displacements measured at d) and g); and assess the stiffness value based on the first and second speeds.

20. The system according to claim 18, wherein the at least one processor calculates a mean stiffness value on a basis of an average between the first and second speeds of the first and second shear wave, respectively.

21. The system according to claim 18, wherein the at least one processor defines the first and second excitation points to be positioned in such a manner that the first and second shear waves passes through the region of interest.

22. The system according to claim 18, wherein the at least one processor measures the first and second displacements by measuring the displacement of the image pixels at a plurality of lines of sight placed in the region of interest at different predetermined laterally staggered distances from the first and second excitation point.

23. The system according to claim 18, wherein the at least one processor obtains one or more reference measurements for a plurality of lines of sight in the region of interest, prior to generating the first and second shear waves.

24. The system according to claim 18, wherein the at least one processor measures the first and second shear waves includes measuring mean displacement over time of the tissue along a plurality of line of sights and identifying a peak of the mean displacements.

25. The system according to claim 18, wherein the at least one processor provides a pause period between a last measurement along one line of sight and a first measurement along a following line of sight.

26. The system according to claim 18, wherein the at least one processor measures the first and second displacements by a cross-correlation between measurements associated with the first and second shear waves and a reference measurement obtained independent of the first and second shear waves.

27. The system according to claim 18, wherein the at least one processor measures displacement over time of the tissue along a plurality of line of sights and calculating speeds of the first and second shear waves based, in part, on distances of the corresponding lines of sight from the first and second excitation points.

28. The system according to claim 18, further comprising a display that displays the ultrasound image with the region of interest shown, and the first excitation point and the second excitation point being further displayed on the ultrasound image.

29. The system according to claim 18, further comprising an ECG unit that records an ECG signal, the at least one processor synchronizing generation of the first and second acoustic disturbance ultrasound beams and the measurement of the first and second displacements of the image pixels induced by the first and second shear waves with the ECG signal.

30. The system according to claim 18, further comprising a filter module configured to analyze an influence of heart movement on the first displacement, the at least one processor managing generation of the second acoustic disturbance ultrasound beam, the filter module configured to apply, to the second measured displacement of the image pixels, a compensation factor based on the influence of the heart movement detected after the first ultrasound beam.

31. The system according to claim 18, wherein the at least one processor makes a correction of longitudinal movement by substracting from each displacement of image pixels a curve having a correction slope calculated by interpolating displacements related to subsequent lines of sight.

\* \* \* \* \*